United States Patent
Mason et al.

(10) Patent No.: US 8,192,684 B2
(45) Date of Patent: Jun. 5, 2012

(54) DECONTAMINATION OF ENCLOSED SPACE USING GASEOUS CHLORINE DIOXIDE

(75) Inventors: John Y. Mason, Odessa, TX (US); Peter Williams, Manchester (GB); Maggie Trabeau, Delmar, NY (US)

(73) Assignee: Sabre Intellectual Property Holdings LLC, Slingerlands, NY (US)

( * ) Notice: Subject to any disclaimer, the term of this patent is extended or adjusted under 35 U.S.C. 154(b) by 227 days.

(21) Appl. No.: 12/769,471

(22) Filed: Apr. 28, 2010

(65) Prior Publication Data

US 2010/0310418 A1 Dec. 9, 2010

Related U.S. Application Data

(60) Provisional application No. 61/184,298, filed on Jun. 4, 2009.

(51) Int. Cl.
 C23F 11/00 (2006.01)
 G01D 11/26 (2006.01)
 A62B 7/08 (2006.01)
 A01M 13/00 (2006.01)

(52) U.S. Cl. ............... 422/37; 422/1; 422/7; 422/28; 422/119; 422/123; 422/305; 43/1; 43/125; 588/299; 588/313; 588/406; 96/227

(58) Field of Classification Search .............. 422/1, 7, 422/28, 37, 119, 123, 305; 43/1, 125; 588/299, 588/313, 406; 96/227
See application file for complete search history.

(56) References Cited

U.S. PATENT DOCUMENTS

| | | | |
|---|---|---|---|
| 4,504,442 A | 3/1985 | Rosenblatt et al. | |
| 4,681,739 A | 7/1987 | Rosenblatt et al. | |
| 5,006,326 A | 4/1991 | Mayurnik et al. | |
| 6,051,135 A | 4/2000 | Lee et al. | |
| 6,605,254 B2 * | 8/2003 | Aguilera et al. | 422/28 |
| 7,571,676 B2 | 8/2009 | Nelson et al. | |
| 2004/0009094 A1 | 1/2004 | Adiga et al. | |
| 2004/0022667 A1 | 2/2004 | Lee et al. | |
| 2005/0019210 A1 | 1/2005 | Rosenblatt et al. | |
| 2005/0031487 A1 | 2/2005 | Rosenblatt et al. | |
| 2006/0228253 A1 | 10/2006 | Mason | |

(Continued)

FOREIGN PATENT DOCUMENTS

WO 03/047640 A1 6/2003

(Continued)

OTHER PUBLICATIONS

International Search Report—PCT/US2010/032812, dated Jan. 19, 2011.

(Continued)

*Primary Examiner* — Jill Warden
*Assistant Examiner* — Monzer Chorbaji
(74) *Attorney, Agent, or Firm* — Heslin Rothenberg Farley & Mesiti P.C.

(57) ABSTRACT

A method for gas phase application of chlorine dioxide within an enclosed volume that includes the steps of: climatizing the enclosed volume to achieve a relative humidity (RH) in the range of about 5% to about 56%; generating chlorine dioxide gas; and introducing the chlorine dioxide gas under specified conditions of chlorine dioxide gas concentration and contact time, the specified conditions being effective to eliminate contaminants within the closed volume, and further to mitigate corrosion within the enclosed volume during the gas phase application.

16 Claims, 18 Drawing Sheets

U.S. PATENT DOCUMENTS

| | | | |
|---|---|---|---|
| 2008/0139869 A1 | 6/2008 | Wilson et al. |
| 2008/0286147 A1 | 11/2008 | Wilson et al. |
| 2009/0081310 A1 | 3/2009 | Mason |
| 2009/0142226 A1 | 6/2009 | McWhorter et al. |
| 2009/0246074 A1 | 10/2009 | Nelson et al. |

FOREIGN PATENT DOCUMENTS

| | | |
|---|---|---|
| WO | 03/077956 A2 | 9/2003 |

OTHER PUBLICATIONS

The Role of Relative Humidity in Corrosion, Jun. 28, 2001.

Muller, C. O., "Control of Corrosive Gases to Avoid Electrical Equipment Failure", Dec. 4, 2003.

Nelson, P.E. "Decontamination of *Bacillus thuringiensis* spores on selected surfaces by chlorine dioxide gas.." *Journal of Environmental Health*, Nov. 1, 2003, 1-7.

Hubbard et al, "Chlorine Dioxide Reactions with Indoor Materials during Building Disinfection: Surface Uptake." *Environmental Science Technology*. vol. 43, No. 5, 2009, 1329-1335.

Busto-Ramo et al, "Development of an online biosensor for in situ monitoring of chlorine dioxide gas disinfection efficacy." *Biotechnological Products and Process Engineering*. Oct. 10, 2007, 573-580.

Wagner et al, "Inactivation of *Stachybotrys chartarum* grown on gypsum board using aerosolized chemical agents." *Journal of Environmental Engineering Science* vol. 5, 2006, 75-79.

Price et al, "Sanitation of Wallboard Colonized with *Stachybotrys chartarum*." *Current Microbiology*. vol. 39, 1999, pp. 21-26.

Hooper et al., "Isolation of Sulfur Reducing and Oxidizing Bacteria Found in Contaminated Drywall." *International Journal of Molecular Sciences*. 2010, pp. 647-655.

Wilson et al., "Fungi and Mycotoxins Associated with Sick Building Syndrome." *American Society of Microbiology*. vol. 71, No. 9, 2005, pp. 5399-5403.

Weaver-Myers et al., "Controlling Mold on Library Materials with Chlorine Dioxide: An Eight-Year Case Study." *The Journal of Academic Librarianship*. Nov. 1998, pp. 455-458.

EPA Research Report EPA/600/R-05/083, Oct. 2005, "Workshop on Decontamination, Cleanup, and Associated Issues for Sites Contaminated With Chemical, Biological, or Radiological Materials.", pp. x-xi, 30.

EPA Research Report EPA/600/R-08/091, Sep. 2008, "Material Demand Studies: Interaction of Chlorine Dioxide Gas With Building Materials."

\* cited by examiner

FIG. 1

Research & Development
Corrosion Study Data Summary

| Analyte | 48% RH 5/19/2009 | 48% RH 5/22/2009 | 54% RH 5/21/2009 |
|---|---|---|---|
| $ClO_2$ (ppm) | 2514 | 2072 | 2202 |
| Chlorite (ppm) | 66 | 128 | 7 |
| $Cl_2$ (ppm) | 1 | 0 | 0 |
| pH | 5.96 | 6.46 | 6.04 |
| Time (hr.) | 6 | 6 | 6 |
| $ClO_2$ (ppm$_v$) | 1523 (± 305) | 1554 (± 469) | 1539 (± 489) |
| CT (ppm$_v$-hrs) | 9090 | 9067 | 8987 |
| Temp (°F) | 75.8 (± 3.0) | 81.1 (± 1.7) | 77.9 (± 1.3) |
| %RH (min) | 42 | 46 | 45 |
| %RH (max) | 51 | 50 | 57 |
| %RH | 48.3 (± 1.7) | 48.5 (± 0.9) | 53.6 (± 3.4) |

FIG. 3

Research & Development
Corrosion Data Summary

| Coupon | 48% CT 9000 | 48% CT 9000 | 53% CT 9000 | 54% CT 9000 | 72% CT 6400 |
|---|---|---|---|---|---|
| Aluminum | No Corrosion | No Corrosion | No Corrosion | No Corrosion | No Corrosion |
| Copper | No Corrosion | No Corrosion | No Corrosion | No Corrosion | No Corrosion |
| Galvanized Steel | Edges Only | Edges Only | Edges Only | Edges Only | Edges Only |
| Galvanized Finishing Nails | No Corrosion | No Corrosion | -- | No Corrosion | -- |
| Steel Finishing Nails | No Corrosion | Very little (spotty) | -- | Severely Corroded | -- |
| Mild Steel | Edges Only (-0.0003 gm) | Edges (powdery) & Some Surface (-0.0007 gm) | Edges & Some Surface (-0.0014 gm) | Surface & Edges (powdery) (-0.0038 gm) | Surface & Edges (very flaky) (-0.0771 gm) |
| Mild Steel (scuffed) | Surface & Edges (-0.0008 gm) | Surface & Edges (very powdery) (-0.0043 gm) | Surface & Edges (flaky) (-0.0456 gm) | Surface & Edges (powdery) (-0.0279 gm) | Surface & Edges (very flaky) (-0.1229 gm) |
| Razor Blade (box cutter) | Slight Spotting | Slight Spotting | Slight Spotting | Corroded (flaky) | Corroded (very flaky) |
| Razor Blade (straight edge) | Slight Spotting | Slight Spotting | -- | Corroded (flaky) - blade only | -- |

Change in weight calculated by subtracting weight after corrosion removal from weight before corrosion removal (post-fume).

| Analyte | 48% CT 9000 5/19/2009 | 48% CT 9000 5/22/2009 | 53% CT 9000 5/8/2009 | 54% CT 9000 5/21/2009 | 72% CT 6400 5/5/2009 |
|---|---|---|---|---|---|
| Chlorine dioxide (ppm) | 2514 | 2072 | 4013 | 2202 | 1970 |
| Chlorite (ppm) | 66 | 128 | 211 | 7 | 20 |
| Chlorine (ppm) | 1 | 0 | -- | 0 | -- |
| pH | 5.96 | 6.46 | 5.92 | 6.04 | 5.78 |
| Exposure Time (hr.) | 6 | 6 | 6 | 6 | 6 |
| Temperature (°F) | 75.8 (± 3.0) | 81.1 (± 1.7) | 78.8 (± 1.2) | 77.9 (± 1.3) | 75.9 (± 0.5) |
| %RH | 48.3 (± 1.7) | 48.5 (± 0.9) | 52.7 (± 2.6) | 53.6 (± 3.4) | 71.9 (± 9.2) |
| lorine dioxide gas ($ppm_v$) | 1523 (± 305) | 1554 (± 469) | 1539 (± 234) | 1539 (± 489) | 1073 (± 443) |
| CT ($ppm_v$-hrs) | 9090 | 9067 | 9004 | 8987 | 6407 |

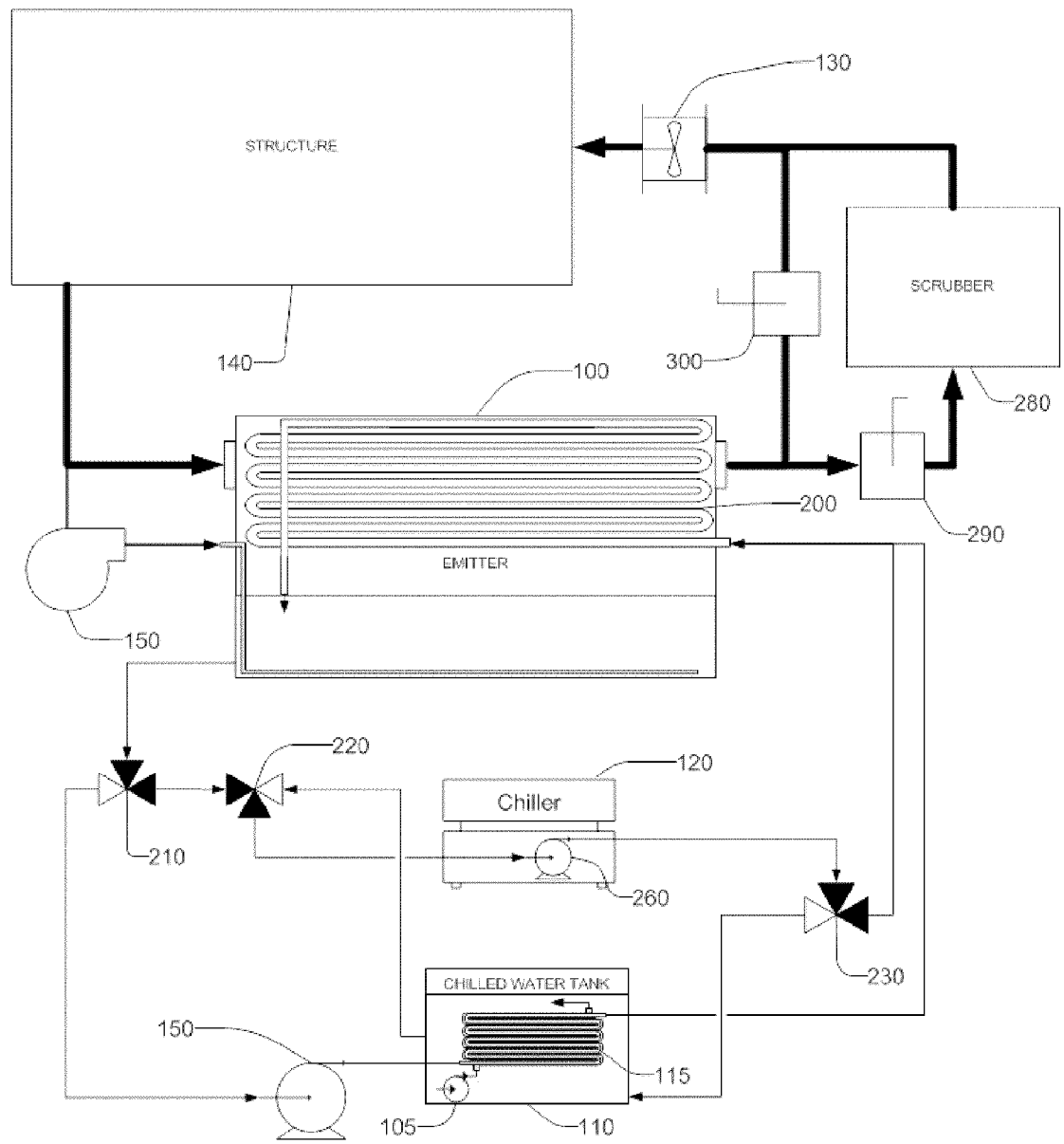
Fig. 7A – Climatization Step

Fig. 7B – Intermediate Step
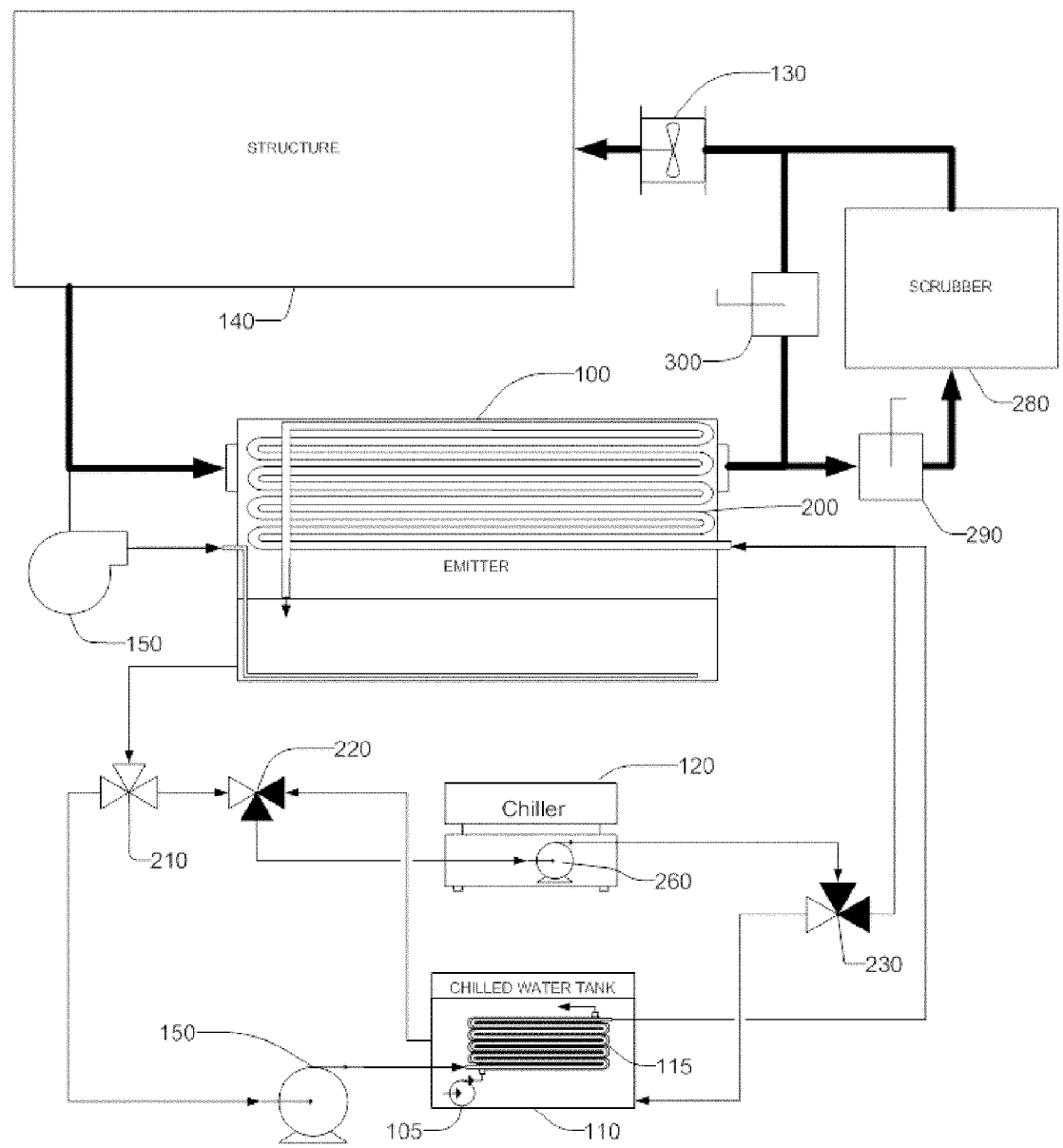

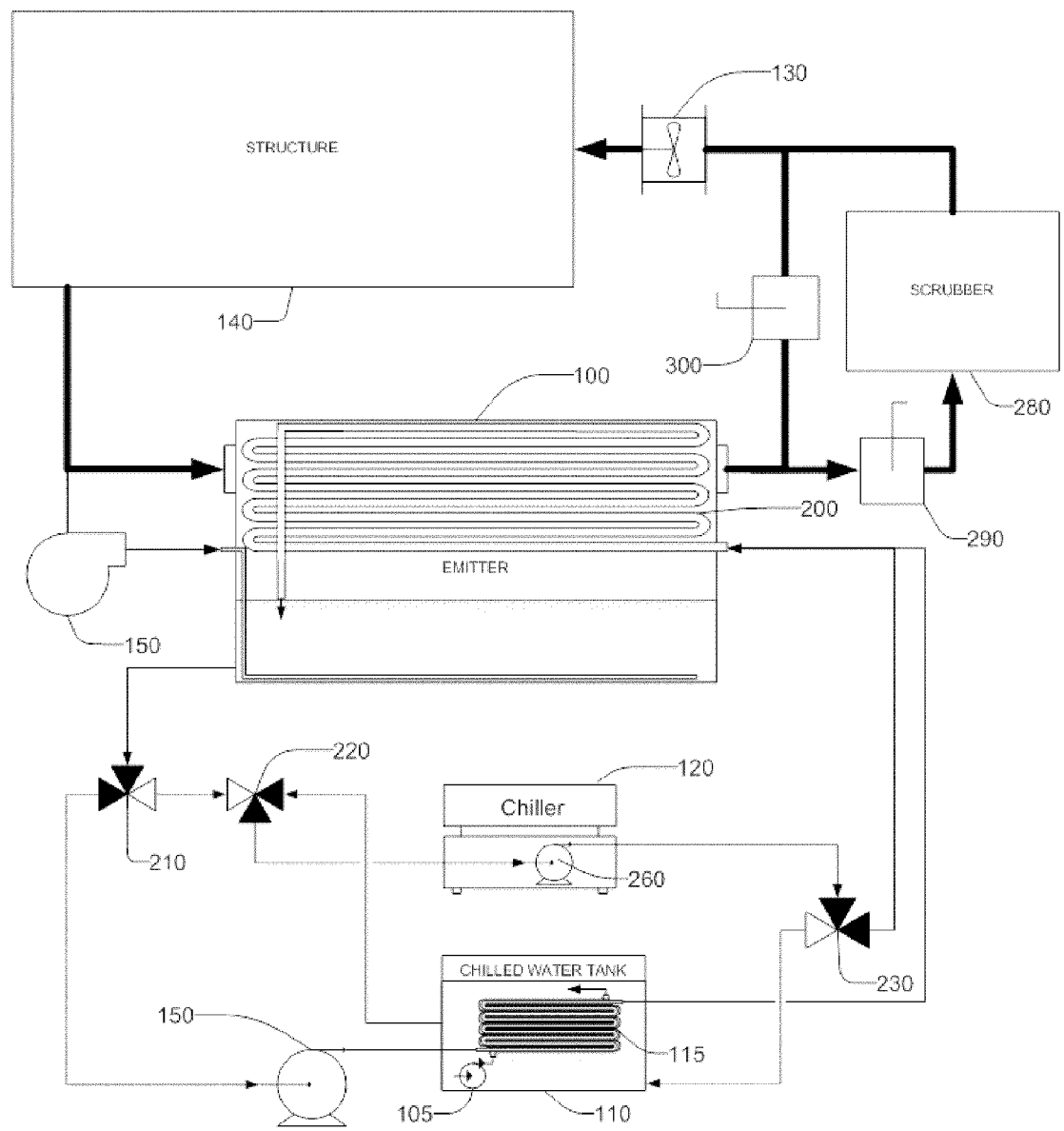
Fig. 7C – Climate Control During Fumigation Step

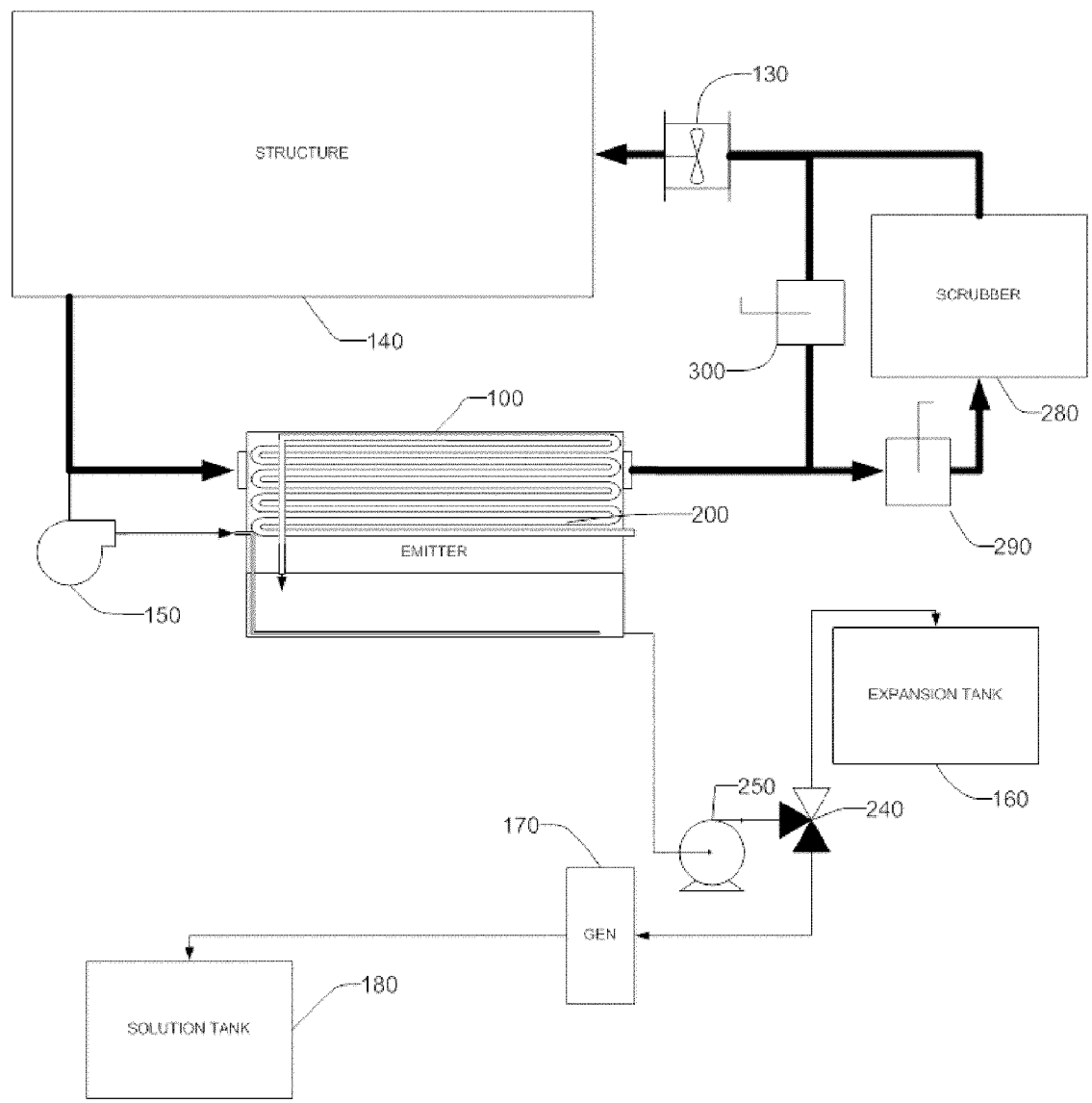
Fig. 8A – Chlorine Dioxide Generation Step

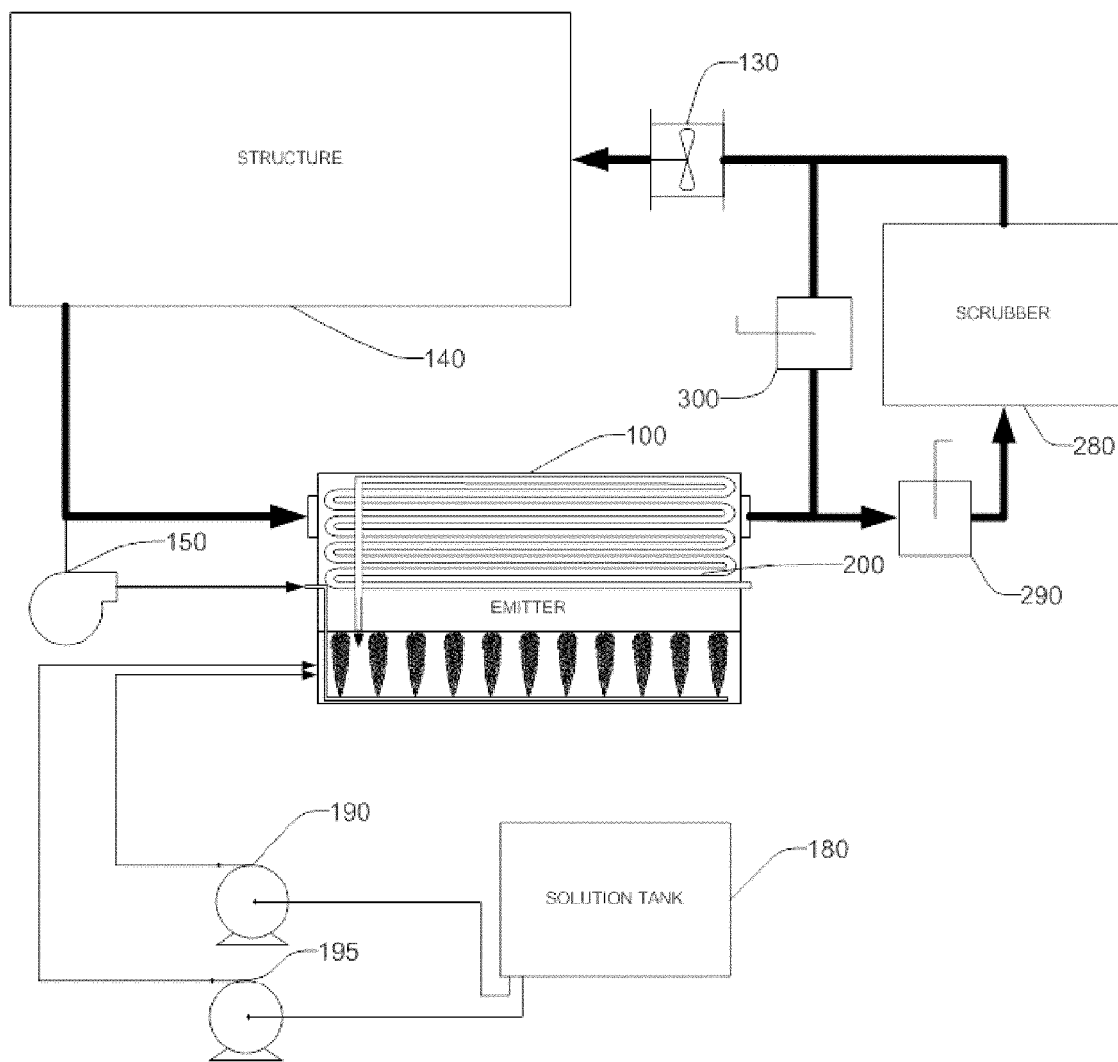
Fig. 8B – Chlorine Dioxide Gas Introduction Step

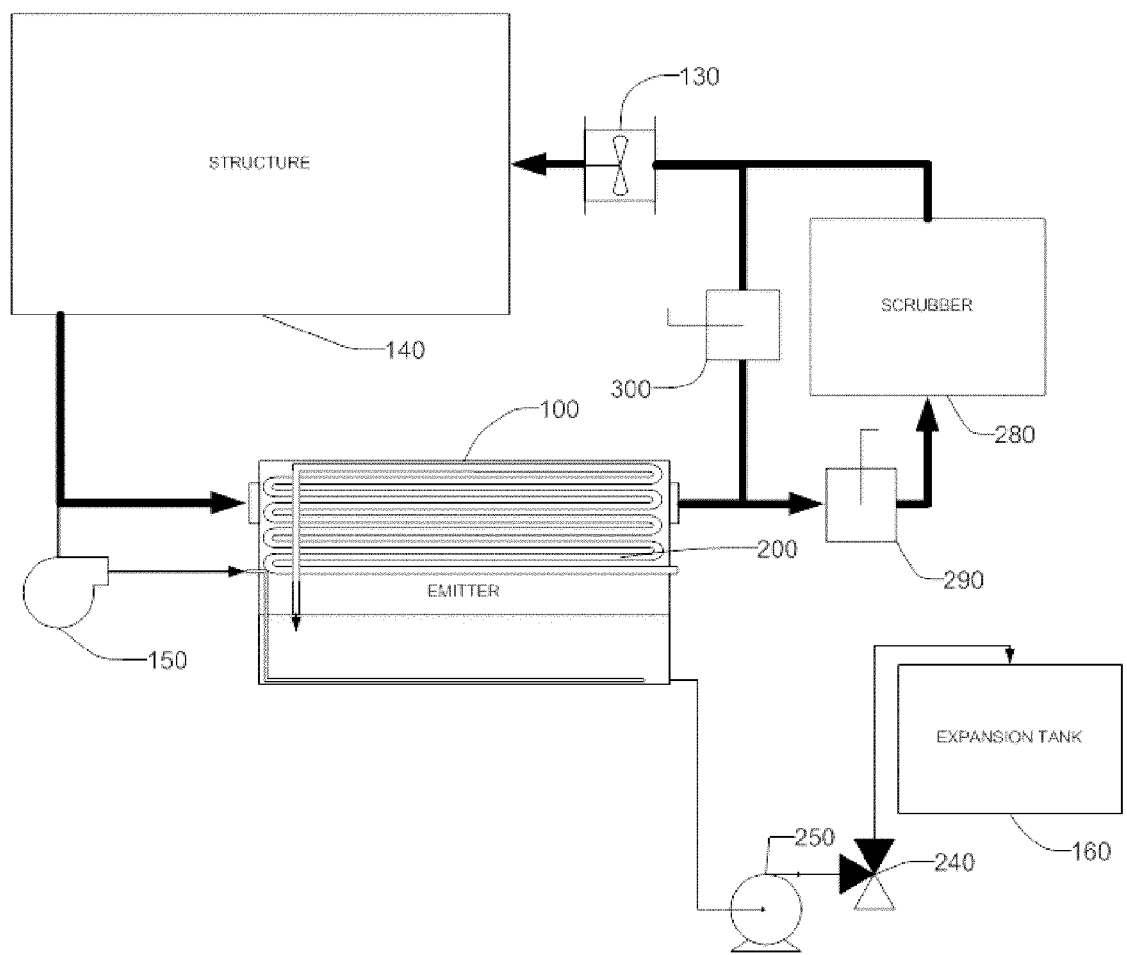
Fig. 8C – Excess Fluid Pump Off Step

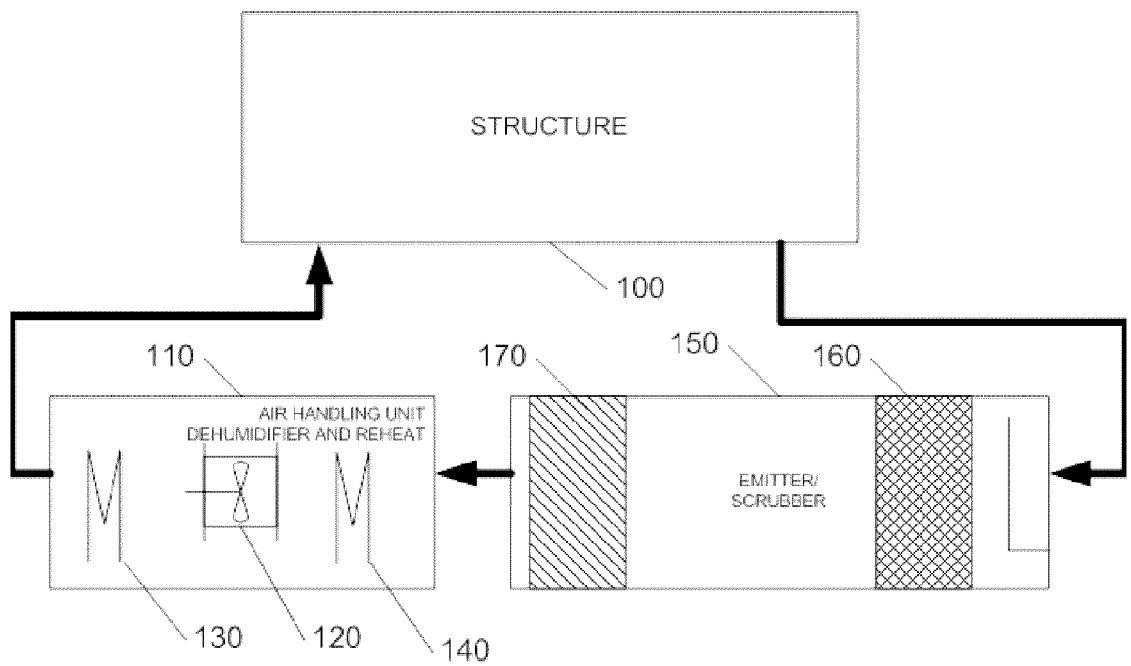
Fig. 9A – Climatization Step

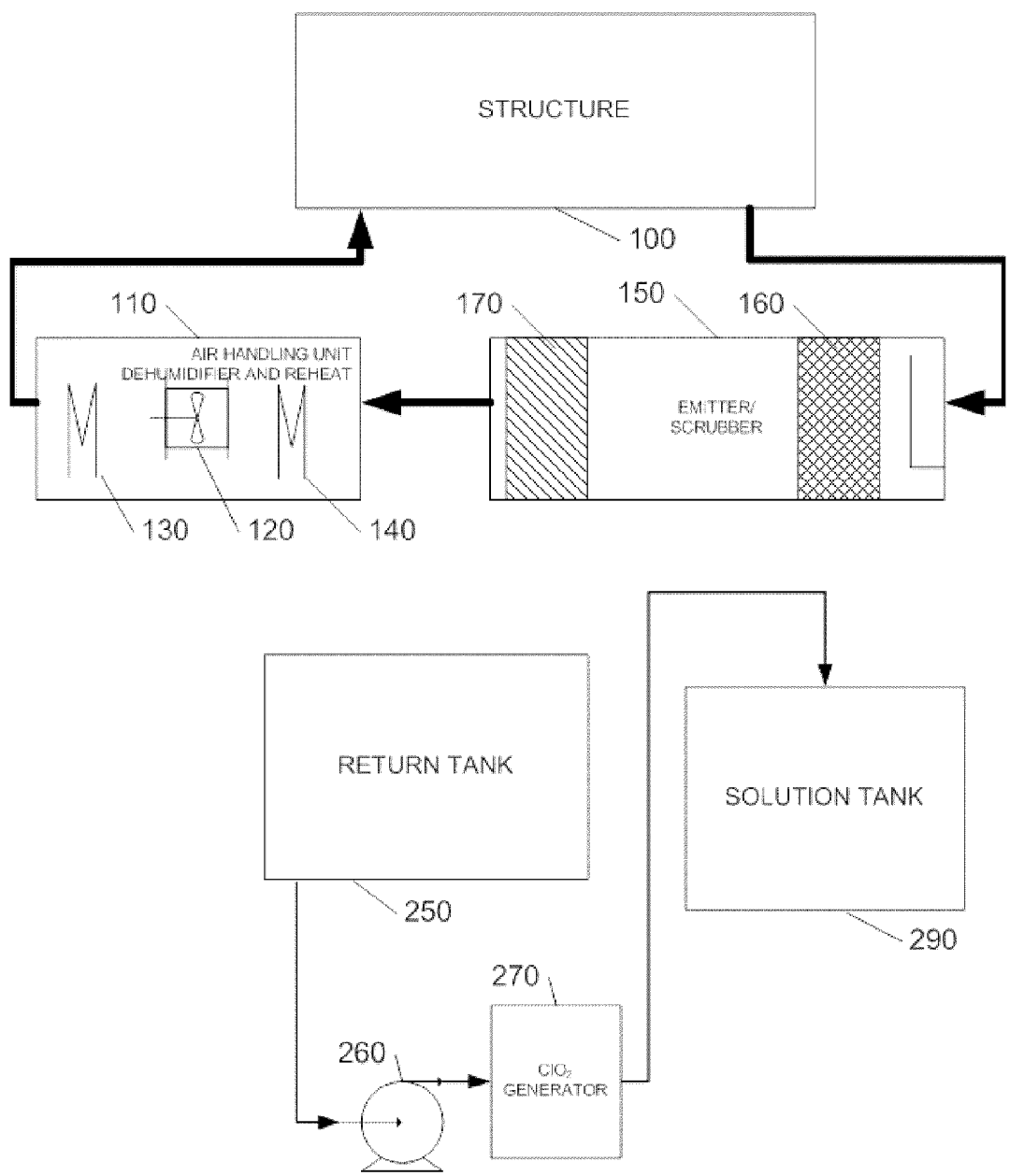
Fig. 9B – Chlorine Dioxide Generation Step

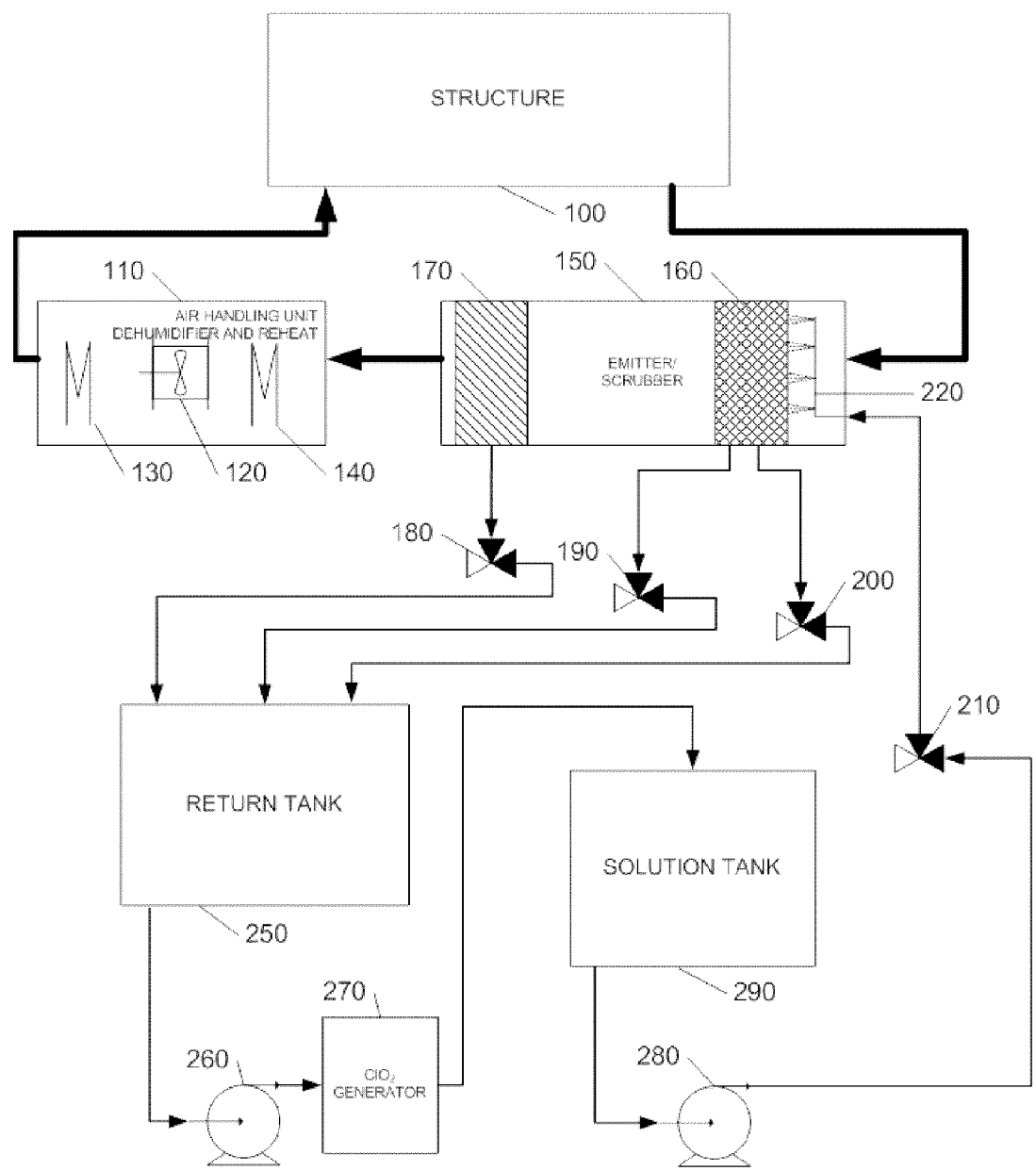
Fig. 9C – Chlorine Dioxide Gas Introduction Step

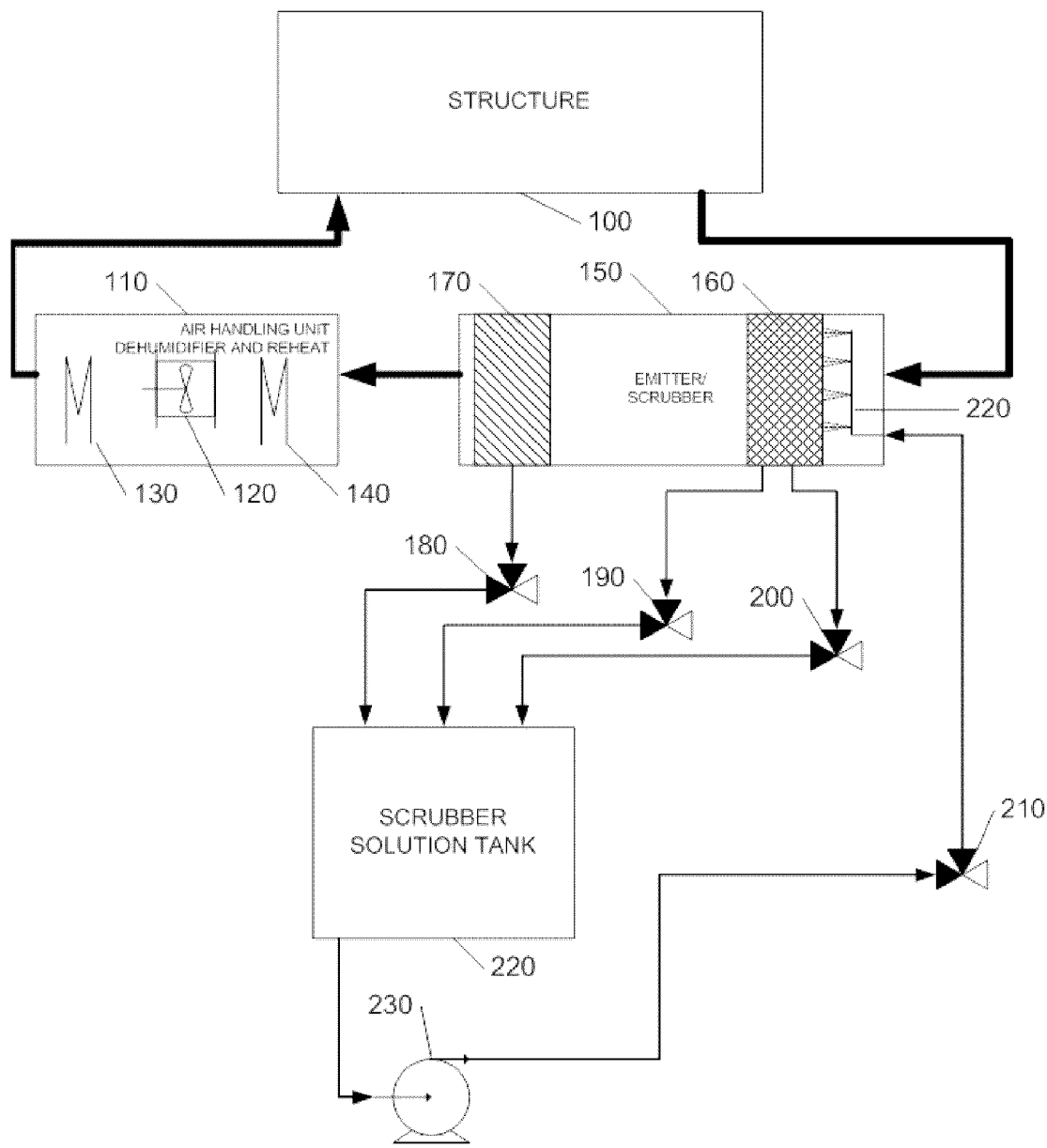

DECONTAMINATION OF ENCLOSED SPACE USING GASEOUS CHLORINE DIOXIDE

CROSS-REFERENCE TO RELATED APPLICATIONS

This application claims the benefit of priority from U.S. Provisional Application No. 61/184,298, filed Jun. 4, 2009.

This application is also related to application Ser. No. Ser. No. 12/769,448, filed herewith, REMEDIATION OF GYPSUM BOARD USING GASEOUS CHLORINE DIOXIDE, the disclosure of which is incorporated herein by reference.

FIELD OF THE INVENTION

The invention relates to a method of remediation or decontamination of an enclosed space using gaseous chlorine dioxide under conditions that mitigate or eliminate corrosion.

BACKGROUND

The use of chlorine dioxide ($ClO_2$) as a sterilizing agent is known. Chlorine dioxide, a powerful oxidant and disinfectant, has been employed in a wide spectrum of gas phase applications, including the disinfection of food, odor control, Anthrax and other microbial decontamination, mold remediation, Chinese wallboard remediation, disinfection of medical waste, and oil and gas injection well stimulation.

For example, chlorine dioxide gas was used in 2001 to decontaminate the Hart Senate Office Building in Washington, D.C., after the discovery of a letter containing *Bacillus anthracis* spores (Anthrax). U.S. patent application Ser. No. 11/270,973 (US Patent Pub. No. 2006/0228253) discloses a method for the large-scale use of chlorine dioxide gas for fumigation and sterilization. Similarly, chlorine dioxide gas has been used to decontaminate mail processing and other commercial buildings in D.C., New Jersey and Florida after the discoveries of anthrax there.

U.S. application Ser. No. 11/576,498 (US Patent Pub. No. 2009/0081310) discloses a method for the effective large-scale use of chlorine dioxide for mold remediation.

U.S. Prov. Appl. Nos. 61/173,844 and 61/252,422 disclose a method for using chlorine dioxide for in situ remediation of gypsum board in existing construction to eliminate sulfate-reducing bacteria and to oxidize reactive metal sulfides in contact with the wallboard.

Despite the numerous successes and general acceptance of chlorine dioxide as a viable fumigant, there is a serious drawback to its widespread use as a gas phase sterilant. Because $ClO_2$ is highly oxidizing, it is prone to exhibit corrosion on certain items located within an enclosed structure upon completion of the fumigation treatment. Although it is well known in the art that chlorine dioxide is less corrosive than chlorine to metals, it has been shown that gas phase application of chlorine dioxide can result in the corrosion of certain metals that are found within a building, either in the structure itself or in the contents located within.

It is an aspect of this invention to mitigate corrosion of the contents within a building, such as electronic equipment (e.g., telephone equipment, computers, copiers, and other electronic office equipment), furnishings, and the like, while still accomplishing successful decontamination using gaseous chlorine dioxide.

SUMMARY OF THE INVENTION

The present invention relates to a method for mitigating corrosion during the gas phase application of chlorine dioxide within an enclosed volume that comprises the steps of: climatizing the enclosed volume to a relative humidity not exceeding about 56%; generating chlorine dioxide gas; and introducing the chlorine dioxide gas into the enclosed volume at an effective concentration-time (CT) value to achieve the desired level of kill of targeted organisms or oxidation of contaminants.

The present invention also relates to a method for gas phase application of chlorine dioxide within an enclosed volume that comprises the steps of: climatizing the enclosed volume to a relative humidity equal to x (%); generating chlorine dioxide gas; and introducing the chlorine dioxide gas into the enclosed volume at a CT value of chlorine dioxide equal to y ($ppm_v$-hrs), wherein y is equal to $6x^2-870x+32100\pm1000$, x being a number between 5 and 56 equal to the % RH.

The present invention further relates to a method for gas phase application of chlorine dioxide within an enclosed volume that comprises the steps of: climatizing the enclosed volume to achieve a relative humidity (RH) in the range of about 5% to about 56%; generating chlorine dioxide gas; and introducing the chlorine dioxide gas at a concentration ranging from 25 $ppm_v$ to 10,000 $ppm_v$ for the appropriate time into the enclosed volume to achieve a CT value of chlorine dioxide equal to y ($ppm_v$-hrs); wherein $y=6x^2-870x+32100\pm1000$, x being a number between 5 and 56 equal to the % RH.

The present invention also relates to a method for gas phase application of chlorine dioxide within an enclosed volume that comprises the steps of: climatizing the enclosed volume to achieve a relative humidity (RH) in the range of about 5% to about 56%; generating chlorine dioxide gas; and introducing the chlorine dioxide gas under specified conditions of chlorine dioxide gas concentration and contact time, the specified conditions being effective to eliminate contaminants within the closed volume, and further to mitigate corrosion within the enclosed volume during the gas phase application.

BRIEF DESCRIPTION OF THE FIGURES

FIG. 1 is a graph summarizing treatment data for a corrosion study at 48% RH and 54% RH.

FIG. 3 is a table summarizing corrosion data for metal objects at various RH values.

FIG. 7 schematically depicts the use of the apparatus depicted in FIG. 6 for control of humidity in the structure; FIG. 7A climatization, FIG. 7B intermediate, and FIG. 7C climate control during fumigation steps in the application of gaseous $ClO_2$.

FIG. 8A schematically depicts the use of the apparatus for the generation of $ClO_2$.

FIG. 8B schematically depicts the use of the apparatus for the introduction of gaseous $ClO_2$ into the structure.

FIG. 8C schematically depicts the use of the apparatus for pumping off excess fluid from the system.

FIG. 9A schematically depicts the use of the apparatus for climatization.

FIG. 9B schematically depicts the use of the apparatus for chlorine dioxide generation.

FIG. 9C schematically depicts the use of the apparatus for the introduction of chlorine dioxide gas to the structure.

FIG. 9D schematically depicts the use of the apparatus for the scrubbing of chlorine dioxide gas from the structure.

DETAILED DESCRIPTION

Figure 2A:
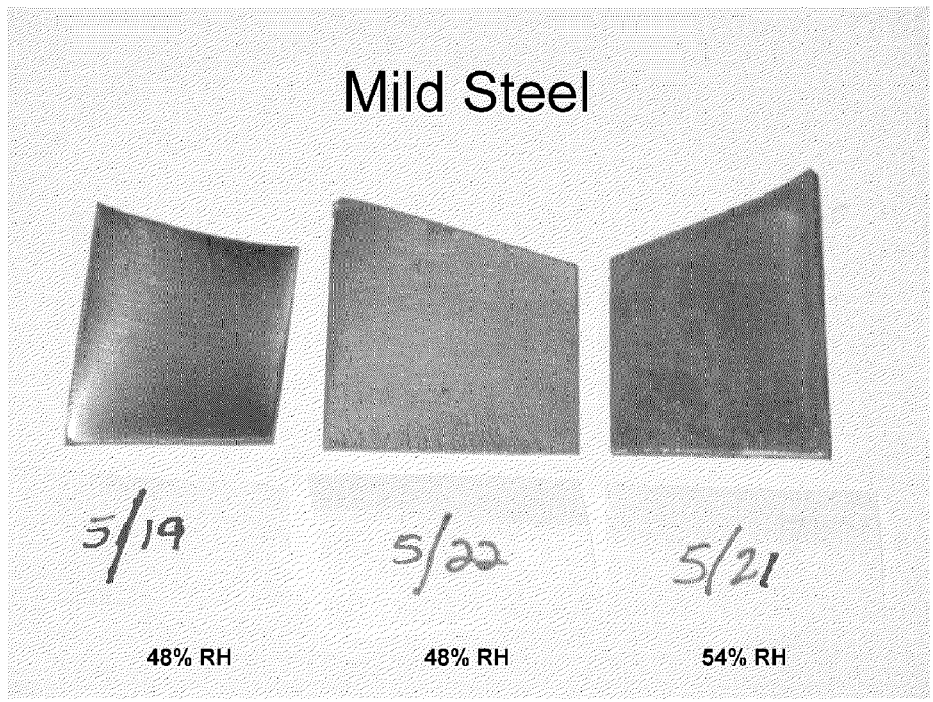
FIGS. 2A-2D are photographs of steel objects subjected to $ClO_2$ at 48% RH and 54% RH.
Figure 2B:
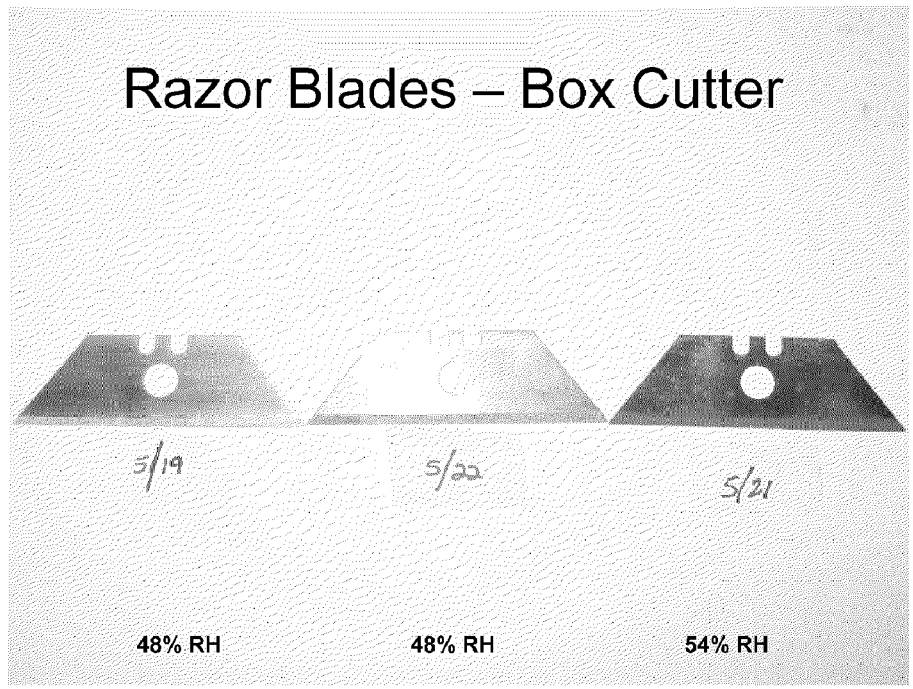
Figure 2C:
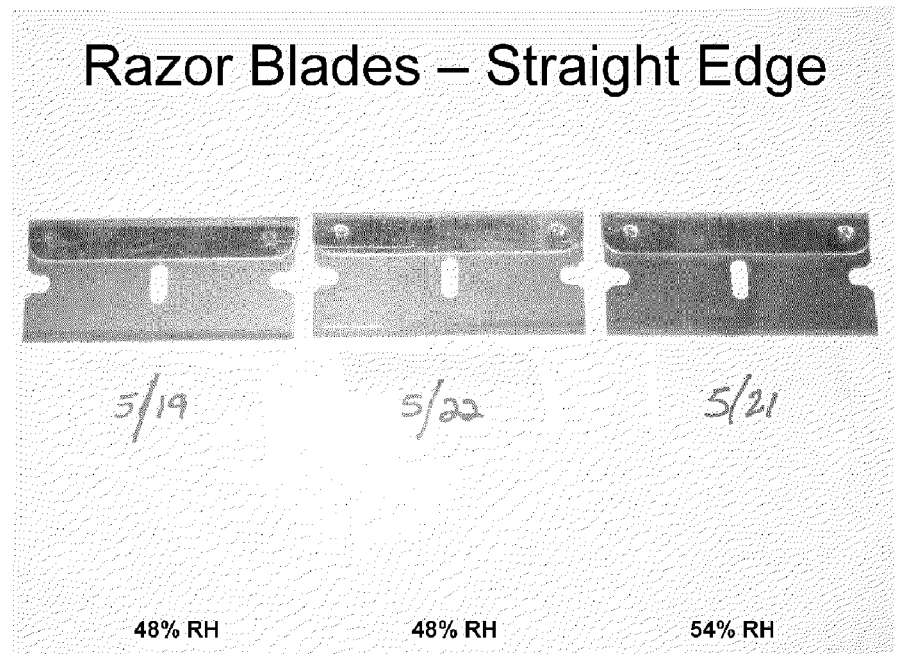
Figure 2D:

Based on past remediation efforts, it is generally accepted that in order to achieve adequate kill, chlorine dioxide fumigation of a building requires a minimum relative humidity (RH) of about 65%, with a target $ClO_2$ concentration and exposure time of 750 $ppm_v$ for 12 hours, for a total concentration of 9000 $ppm_v$-hrs (CT). Other researchers have recommended a RH of greater than 70% for $ClO_2$ concentrations between 125 and 10550 $ppm_v$. Under current EPA guidelines, applications of $ClO_2$ for building remediation require 75% relative humidity and an exposure of 9000 $ppm_v$-hrs.

An EPA report issued September 2008, entitled Material Demand Studies: Interaction of Chlorine Dioxide Gas with Building Materials, described glove box tests carried out at RH above 75% and a temperature above 25° C. on samples of carpet, painted steel, gypsum wallboard, ceiling tile, wood, and concrete. Concentrations of chlorine dioxide of 1000 $ppm_v$ and 2000 $ppm_v$ were employed, with a target CT of 12,000 $ppm_v$-hrs. The chlorine dioxide demand varied with the type of building material, but significant operational problems were encountered during the tests, the result of corrosion of electronic components, flow meters, and pumps. Corrosion was also observed on the stainless steel parts within the test chamber.

In the method of the present invention for gas phase application of chlorine dioxide within an enclosed volume to accomplish elimination of contaminants and mitigate corrosion therein, the enclosed volume is climatized to achieve a relative humidity (RH) in the range of about 5% to about 56%, preferably about 35% to about 53%, more preferably about 40% to about 52%, still more preferably about 45-50%, most preferably about 45% to about 48%. Climatizing the enclosed volume is carried out at a temperature of about 10° C. (50° F.) to about 32° C. (90° F.), preferably about 18° C. (65° F.) to about 29° C. (85° F.). "Elimination of contaminants" is defined as eliminating at least 95% of contaminants, or preferably eliminating at least 98% of contaminants, or more preferably eliminating at least 99% of contaminants.

The contaminants within the enclosed volume may be selected from the group consisting of: bacteria, spores, molds, mycotoxins, allergens, insects, larvae, arachnids, lizards, and combinations thereof. The enclosed volume may include objects selected from the group consisting of metallic objects, non-metallic objects, and combinations thereof.

Metallic objects within the enclosed volume may be formed from metals selected from the group consisting of steel, aluminum, iron, copper, chromium, lead, and combinations thereof. Non-metallic objects may be formed from materials selected from the group consisting of wood, brick, stone, cinder concrete, ceramic tile, ceiling tile, carpet, woven fabric, and combinations thereof.

In one embodiment of the invention, the chlorine dioxide gas is introduced into the enclosed volume at a CT value of chlorine dioxide equal to y ($ppm_v$/hrs), wherein $y=6x^2-870x+32100\pm1000$, x being equal to % RH. In a further embodiment, the chlorine dioxide gas is introduced into the enclosed volume at a CT value of about 29,000 $ppm_v$-hrs to about 1000 $ppm_v$-hrs. In still another embodiment, the chlorine dioxide gas is introduced into the enclosed volume at a concentration of about 25 $ppm_v$ to about 10,000 $ppm_v$, preferably about 500 $ppm_v$ to about 30,000 $ppm_v$.

In another embodiment of the invention, the method for mitigating corrosion during gas phase application of chlorine dioxide within an enclosed volume comprises the steps of: climatizing the enclosed volume to achieve a relative humidity in the range of about 5% to about 56%, and introducing chlorine dioxide gas into the enclosed volume at a CT value of about 1000 $ppm_v$-hrs to 29,000 $ppm_v$-hrs.

Corrosion Mitigation Experiments During Gas Phase Application of $ClO_2$

As used herein, "CT", or total concentration, equals the time-weighted average of chlorine dioxide concentration multiplied by the exposure time in hours. In a plot of chlorine dioxide concentration versus exposure time in hours, the CT would equal the area under the curve. For example, if the time weighted average chlorine dioxide concentration over a 12-hour exposure period were 750 $ppm_v$, the CT would be 9000 $ppm_v$-hrs.

In a gas or vapor phase application of chlorine dioxide, typical chlorine dioxide concentrations are in the range of 500 to 3000 $ppm_v$, and exposure times are typically about 8 to 12 hours. For example, a time averaged chlorine dioxide gas concentration in the range of about 500 to 1500 $ppm_v$ over a 12 hour period has been found effective for killing mold spores and eliminating allergenic effects (CT=6000-18000 $ppm_v$-hrs). Similarly, a CT of 9000 $ppm_v$-hrs has been found effective for sterilizing anthrax.

Based on these ranges of chlorine dioxide concentrations, laboratory corrosion studies were conducted in a $ClO_2$ exposure chamber in a laboratory. As seen in FIG. 1, the corrosive effect of chlorine dioxide on a select group of materials was determined at an average relative humidity of 48%, 53%, 54%, and 72%. At RH equal to 48%, 53%, and 54%, the studies were performed over a 6-hour time period using a concentration of chlorine dioxide sufficient to achieve a total concentration of chlorine dioxide equal to approximately 9000 CT ($ppm_v$hrs) for each sample. (See FIGS. 1 and 3). At RH equal to 72%, a concentration of chlorine dioxide was used sufficient to achieve a total concentration of chlorine dioxide equal to approximately 6400 CT ($ppm_v$hrs). (See FIG. 3). The samples tested comprised aluminum; copper; galvanized steel; galvanized finishing nails; steel finishing nails; razor blades from a box cutter; razor blades from a straight edge razor; mild steel; and mild steel (scuffed).

In performing the corrosion tests, the target set points for each desired % RH level were as follows:

| Target % RH | Reheat Column/Chamber Temperature (° F.) | Chamber $H_2O$ Bath (° C.) | Stripper Column Temperature (° F.) | Stripper Column $H_2O$ Bath (° C.) |
|---|---|---|---|---|
| 45 | 70 | 20 | 48 | 0.5 |
| 55 | 70 | 20 | 53 | 7 |
| 65 | 70 | 20 | 58 | 11 |

When the % RH needed to be lowered, the stripper column temperature was lowered. If the % RH needed to be raised, the stripper column temperature was raised. These temperature adjustments were done using the stripper column $H_2O$ bath. The opposite holds true for the reheat column/chamber. If the % RH needed to be lowered, the reheat column temperature was raised. If the % RH needed to be raised, the reheat column temperature was lowered. One must keep in mind that adjusting this set-point also affects the chamber temperature. All temperature adjustments were done using the reheat column/chamber $H_2O$ bath.

First, both water baths were turned on and adjusted to desired set-points as set forth above. Then, the stripper column pump and chamber blowers were turned on. The stripper column was filled with cold tap water up to the drain line and the chamber hatch left open as the stripper column $H_2O$ bath chilled down to its set-point. Typically it took about 2 hours for the water bath to chill down. Once the set points were reached, the samples were placed in chamber and the hatch closed. To introduce $ClO_2$, tap water was simultaneously emptied from the stripper column while charging it with $ClO_2$ solution until it reached the drain line and fumigation would begin. While fumigating, the column was periodically charged with fresh $ClO_2$ to reach desired concentrations and to maintain concentrations. The flow rate of chlorine dioxide solution was set at 800 mL/hour. When ready to end the fumigation, both of the evacuation ports were opened and a vacuum nozzle placed on the port farthest from the stripper column. While evacuating the chamber, the stripper column was flushed with fresh tap water until the water coming out of stripper column was clear. The samples were removed. Results from the corrosion test can be seen in FIGS. 2A-2D, 3, and 4.

Figure 4:
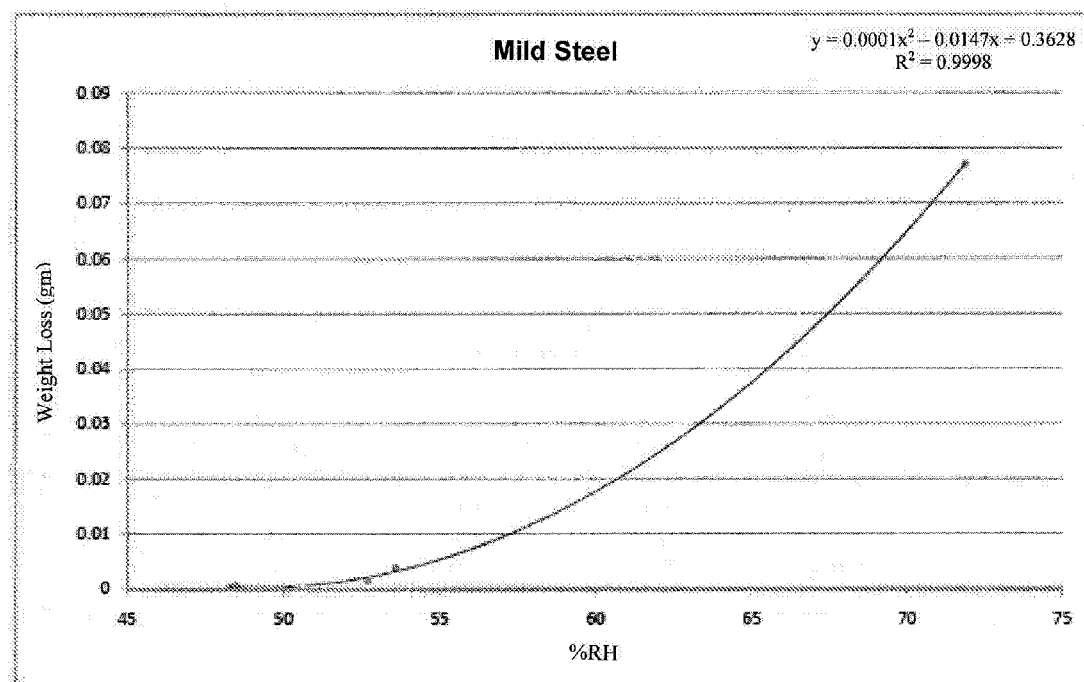
FIG. 4 is a plot of weight loss as a function of RH for mild steel.

As shown in FIG. 3, regardless of RH or concentration of $ClO_2$, little to no corrosion was seen in the aluminum, copper, galvanized steel, or galvanized finishing nails. In contrast, during gas phase application of chlorine dioxide, relative humidity is directly related to the amount of corrosion that occurs on steel finishing nails; razor blades from a box cutter; razor blades from a straight edge razor; and mild steel. (See FIGS. 2A-2D and 3). In other words, as the RH increases, the amount of corrosion increases. The corrosion weight loss exhibited in mild steel exposed to chlorine dioxide gas at increasing RH is shown in FIG. 4.

Testing for Acceptable Kill Levels at Target RH

Figure 5:
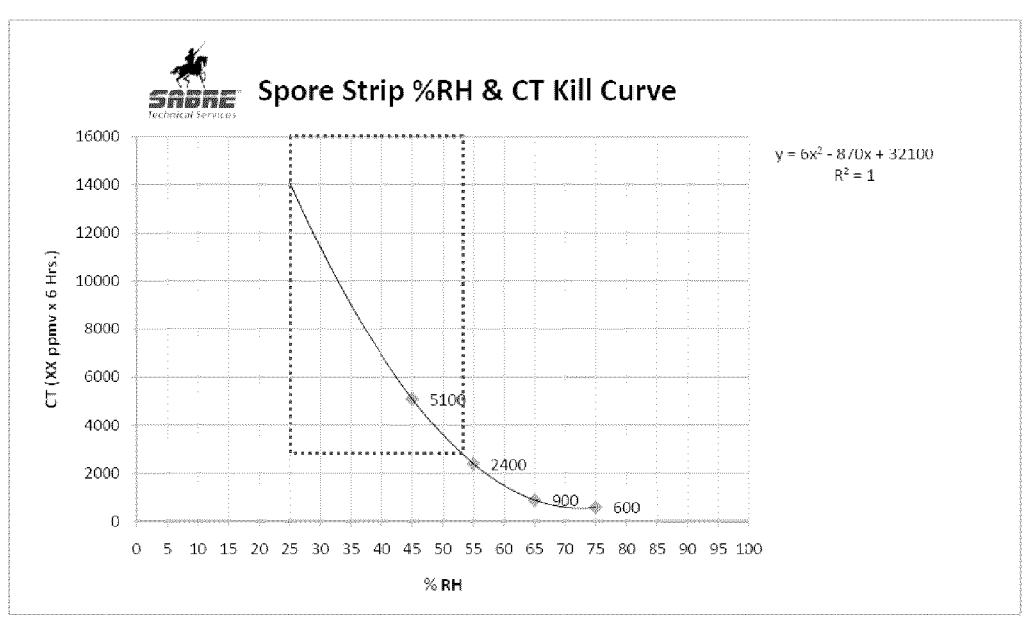
FIG. 5 is a plot of spore strip kill rate as a function of CT and RH.

Laboratory studies were conducted to establish relative humidity and temperature test conditions. As seen in FIG. 5, the kill rates using chlorine dioxide were determined at an average relative humidity of 45%, 55%, 65% and 75%. Paper strips containing 106 *Bacillus atrophaeus* spores (spore strips) were placed in the fumigation chamber. The chamber and the test strips were allowed to stabilize for a minimum of one hour maintaining the target relative humidity and temperature conditions. Chlorine dioxide gas was then introduced to the chamber while maintaining these conditions for the specified concentration and time (CT) to meet the test conditions. The spore strips were then recovered and cultured to determine kill.

As can be seen in FIG. 5, a six log kill was achieved according to the following equation $y=6x^2-870x+32100\pm1000$, wherein x is equal to relative humidity (%) and y is equal to CT, i.e. total concentration of chlorine dioxide ($ppm_v$-hrs).

As can also be seen in FIG. 5, at a RH of 45%, a six log kill can be achieved with a total concentration of chlorine dioxide equivalent to 5100 CT (ppmvhrs). A CT of 5100 $ppm_v$hrs is well within the range of acceptable chlorine dioxide levels as established by those of ordinary skill in the art and governmental agencies that set the standards for fumigation using chlorine dioxide. In fact, it is customary for the gas phase application of chlorine dioxide to use a CT of 9000 ppmv-hrs. A six log kill was achieved at a RH of approximately 35% using a CT of 9000 ppmv-hrs.

Climatization of Enclosed Space to be Fumigated to Achieve Target RH

In contrast to prior gas phase applications of chlorine dioxide, which call for a high relative humidity (i.e. within the range of 65-70%) in the enclosed space to be fumigated, in this improved method it is necessary to achieve a target low humidity (approximately 45%). Prior to fumigation, an emitter may be used with water alone to lower (or raise, in some instances) the relative humidity in the volume requiring remediation. This is done by adjusting the temperature within the system and, in a preferred embodiment, is accomplished as follows.

Figure 6:
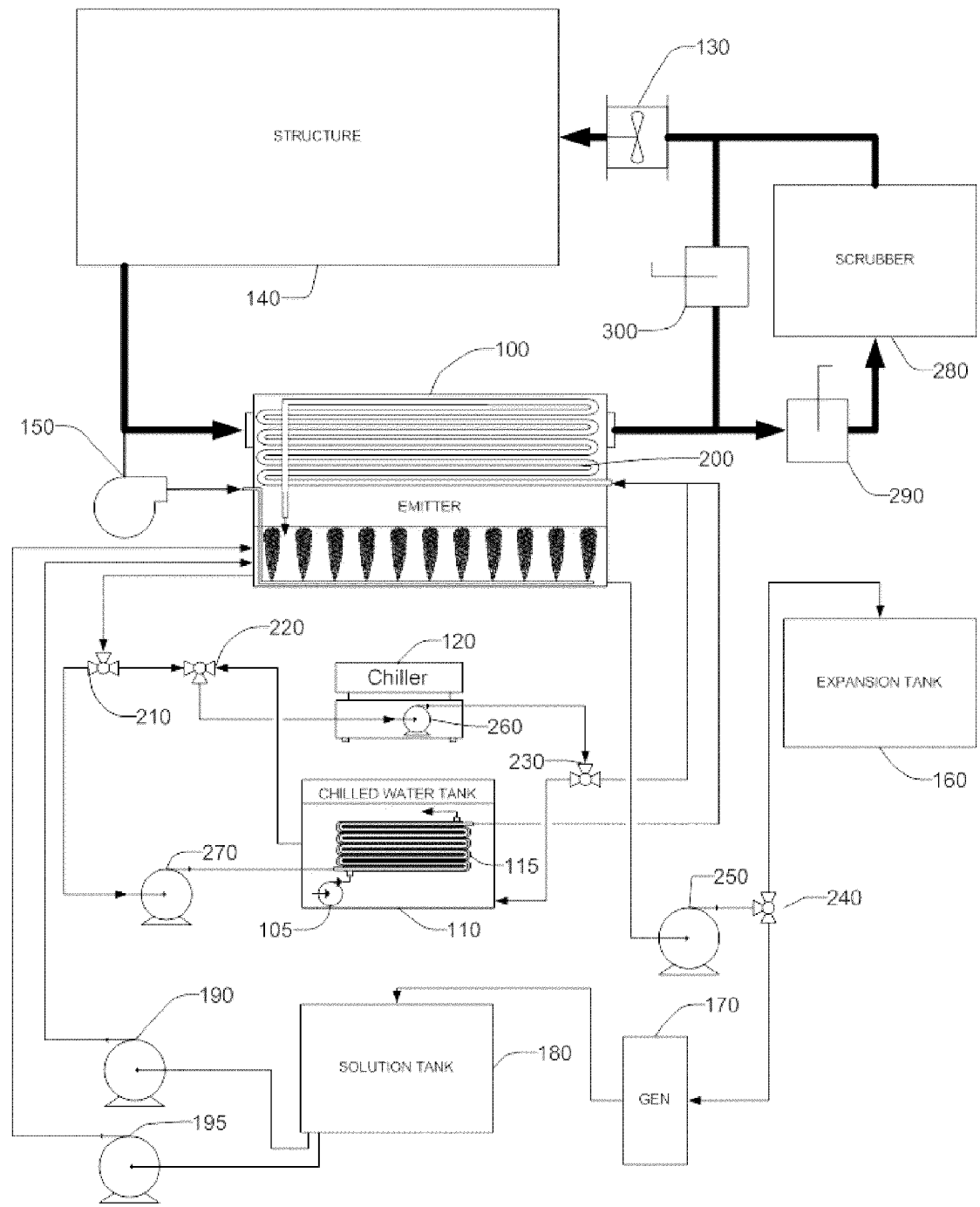
FIG. 6 is a schematic diagram of apparatus suitable for use in the method of the invention.

The present invention can be further understood by reference to FIGS. 6-8, which schematically illustrates one embodiment of the invention. In a preferred embodiment, lowering the relative humidity in an enclosed space or structure such as a building or home can be accomplished by the use of an emitter and a chiller. First, referring to FIG. 6, a volume of water is placed in emitter 100. In a preferred embodiment, approximately 2-3 feet of water is placed in the bottom of emitter 100. This water is then passed through chiller 120 to take the temperature of the water down to the appropriate dew point temperature when compared to the temperature of building 140. For example, if the temperature in the building 140 or other enclosed space to be fumigated is 75° F., a dew point temperature of about 52° F. is needed in the water.

To achieve this temperature, the water is initially circulated out of the emitter 100 through a chiller 120 using a pump 260 that continually chills the water. The chilled water flows back into the emitter through a series of 'condenser' pipes 200 in the air space above the water in the emitter (FIG. 7A).

Once the target dew point temperature in the emitter 100 is reached, the target humidity in the enclosed space to be fumigated is reached by passing the air from the building 140 using a fan 130 through emitter 100. Due to the cold water at dew point temperature circulating through the condenser pipes in the emitter, the humidity in the air passed through the emitter 100 will drop as water vapor is condensed out of the air.

The de-humidified air will then go back into the building 140. This process is continued in a cycle until the target relative humidity in building 140 is achieved, and then fumigation can begin.

In other words, in the initial stage before fumigation begins, the valve configuration (210, 220, 230) of the system allows all of the water in the emitter 100 to pass directly through the chiller 120, which brings the water in the emitter 100 down to the required dew point temperature. Using this configuration, water is kept circulating through the condenser coils 200 in the top of the emitter 100, while air is pumped from the building using a fan 130 through the top space in the emitter, such that air passes over the cold condenser coils 200.

Once the target relative humidity is reached in building 140, fumigation can start. The valve configuration (220, 230) in the system is then switched over so that the chiller 120 is controlling the temperature of water in a separate tank 110 containing a double wall counter flow heat exchanger 115 (FIG. 7B). This is done to avoid having to put the chlorine dioxide solution directly through the chiller 120. During the fumigation process, as described in more detail below, chlorine dioxide solution is injected into the emitter 100 where the bubbling air through the water in the emitter 100 strips the gas out and then carries it into the building 140. The water in the emitter is continuously passed through the heat exchanger 115, which is sitting in the middle tank 110 of cold water that is kept cold by the chiller 120. This maintains the dew point temperature of the water in the emitter.

Referring to FIG. 7, first the valves in the system are configured for the Climatization Step (7A). In this initial start up step, the water is going directly from the emitter to the chiller and air is passed from the building to the emitter to de-humidify it. In Intermediate Step (7B), the valves are configured so that the chiller cools the middle tank of water 110 that holds a heat exchanger 115 to about dew point temperature. To accomplish this, water moves from chiller 120 to middle tank 110 and then back to the chiller 120. Finally, in Climate Control During Fumigation Step (7C), the valves (210, 220, 230) are configured such that water from the emitter 100 is pumped through the heat exchanger 115 sitting in middle tank 110. The water circulating from emitter 100 passes through the heat exchanger in middle tank 110, while the water in middle tank 110 is kept at about dew point by chiller 120. The cold water in the middle tank 110 is continuously circulated in a counter flow through the heat exchanger by a small submersible pump 105 in the middle tank 110 for maximum cooling efficiency.

As also shown in FIG. 6, the system's air loop is under balanced pressure. This is accomplished by the use of fan 130, which draws air (via suction) from building 140 through the emitter 100 and scrubber 280, then back in again. In a preferred embodiment, fan 130 operates at about 5000 cubic feet per minute (CFM). In addition, blower 150 takes a small amount of air from the building 140 and passes it through the water in emitter 100 in order strip the chlorine dioxide gas. In a preferred embodiment, blower 150 operates at about 100 CFM.

For the fumigation step, referring to FIG. 8, water is pumped from the emitter 100 by a pump 250 through a chlorine dioxide generator 170 and into a solution holding tank 180 (FIG. 8A). The solution is then pumped from the solution holding tank 180 into the emitter 100 using pump 190 (FIG. 8B). Pump 200 is used as a backup pump to increase the flow of solution to the emitter if required. Chlorine dioxide is stripped from the solution in the emitter 100 by means of the blower 150 blowing air through the water in the emitter.

Finally, as chemicals are introduced into the system to generate chlorine dioxide, the volume of aqueous solution in the system increases. Therefore, in order to maintain a constant volume in the emitter, it is advantageous to provide for waste storage tank 160 into which excess fluid can be pumped from the system by pump 250 through valve 240 in order to remove volume from the system.

The entire system in FIGS. 6-8 is designed to both pump gas into the building and to maintain the target relative humidity within the building. In one embodiment, this is accomplished by keeping the air in the emitter at the dew point temperature. According to this embodiment, when the air enters the building, it will be warmed because of the higher temperature in the building (e.g., about 75° F.). As the temperature of the air from the emitter rises, the relative humidity will drop. In other words, the air in the emitter is at dew point so that any gas that is bubbled through and pumped into the building is essentially at saturation (100% RH). When this enters the building and warms up, the humidity will drop to the target RH.

When the required concentration of chlorine dioxide gas has been reached in the structure, and maintained for the required time to achieve the target CT, the gas is removed from the air in the building. This is achieved by closing damper 300 and opening damper 290 and passing the air through a scrubber 280. The scrubber can be a container of activated carbon, or a liquid scrubber using an alkalizing and dechlorinating agent or other functional chemistry (e.g., ascorbic acid). The air is continuously circulated through the scrubber until the measured concentration of chlorine dioxide gas in the air in the structure has been reduced to below the target concentration.

The present invention can be further understood by reference to FIG. 9, which schematically illustrates a further embodiment of the invention. In this further embodiment, lowering the relative humidity in an enclosed space or structure such as a building or home, and introducing chlorine dioxide gas to the structure can be accomplished by the use of an emitter/scrubber, which functions as both an emitter and a scrubber, and an air handling unit which functions both as a dehumidifier and air reheat unit.

First, referring to FIG. 9A, air is pulled under suction from the structure 100, through the emitter/scrubber 150, through the air handling unit 110 and recirculated back into the structure by means of a fan 120. The fan 120, which may be part of or separate from the air handling unit, may be placed at any point in the air re-circulation loop.

During recirculation of the air through the air handling unit 110, a refrigeration coil 140 is set at a temperature sufficient to remove moisture from the air and thereby achieve the target relative humidity. The air passing over the coil 140 is effectively chilled to a temperature near to that of the coil. The relative humidity of the air leaving the coil is approaching 100% at this point. In order to achieve the desired relative humidity in the air leaving the air handling unit 110, the air is reheated to the temperature of the air in the building with a heating coil 130. The reheat coil may be electrical, or may use waste heat from the refrigeration process, or a combination of both.

The refrigeration and reheat capacity of the air handling unit may be sized to achieve the desired target relative humidity with one pass of the air through the air handling unit, or to achieve the desired target relative humidity after two or more passes of the air through the air handling unit.

As also shown in FIG. 9A, the system's air loop is under balanced pressure. This is accomplished by the use of fan 120, which draws air (via suction) from the structure 100, through the emitter/scrubber 150, through the air handling unit 110, and then back into the structure. In this embodiment, fan 120 operates at a preferred flow rate of about 3000 cubic feet per minute (CFM). Fan 120 may operate at any flow rate provided that it does not exceed the air flow rate design parameters of the refrigeration coil 140 or the reheat coil 130.

For the chlorine dioxide solution generation step, referring to FIG. 9B, first water is added to the return tank 250 in a sufficient volume to meet the needs of the chlorine dioxide generation process. In this embodiment, the preferred volume is about 250 US gallons. Pump 260 is switched on to pump the water from return tank 250, through the chlorine dioxide generator 270, and into the solution tank 290. This continues until all the water in return tank 250 has been transferred through the generator 270 into the solution tank 290.

For the chlorine dioxide gas introduction step, referring to FIG. 9C, the air flow through the emitter/scrubber 150 and air handling unit 110 is maintained by fan 120 with both the refrigeration coil 140 and the reheat coil 130 functioning, so that any humidity introduced in the air stream by the emitter/scrubber is removed before the air is returned to the structure.

To introduce chlorine dioxide gas to the air flow, the emitter/scrubber first has to be configured to function as an emitter. The valves 180, 190 and 200 on the emitter/scrubber drains are configured so that any liquid draining from the emitter/scrubber drains back into the return tank 250. Valve 210 is then configured so that fluid from pump 280 is directed through the spray header bar 220 in the emitter/scrubber 150.

With air flowing through the emitter/scrubber, pump 280 is turned on to send chlorine dioxide solution to the emitter/scrubber through the spray head 220. An impingement bank 160 in the emitter/scrubber ensures intimate contact between the chlorine dioxide solution and the air. This contact enables chlorine dioxide gas to be released from the solution and enter the air stream.

Depleted chlorine dioxide solution drains from the emitter/scrubber 150 back into the return tank 250 via valves 190 and 200. A mist eliminator 170 is utilized to remove water droplets from the air leaving the emitter scrubber. Liquid taken from the air by mist eliminator 170 drains back into the return tank 250 via valve 180.

The depleted chlorine dioxide solution is then pumped from the return tank 250 through the chlorine dioxide generator 270 by pump 260 into the solution tank 290. This recharges the spent solution with chlorine dioxide ready for return to the emitter/scrubber by pump 280. This process continues until the required concentration of chlorine dioxide has been reached in the structure and held for the required time at that concentration to achieve the target CT.

When the required concentration of chlorine dioxide has been maintained in the structure for the required time period to achieve the target CT, pump 280 is turned off and the scrubbing process to remove the chlorine dioxide gas from the structure can commence.

Figure 9:
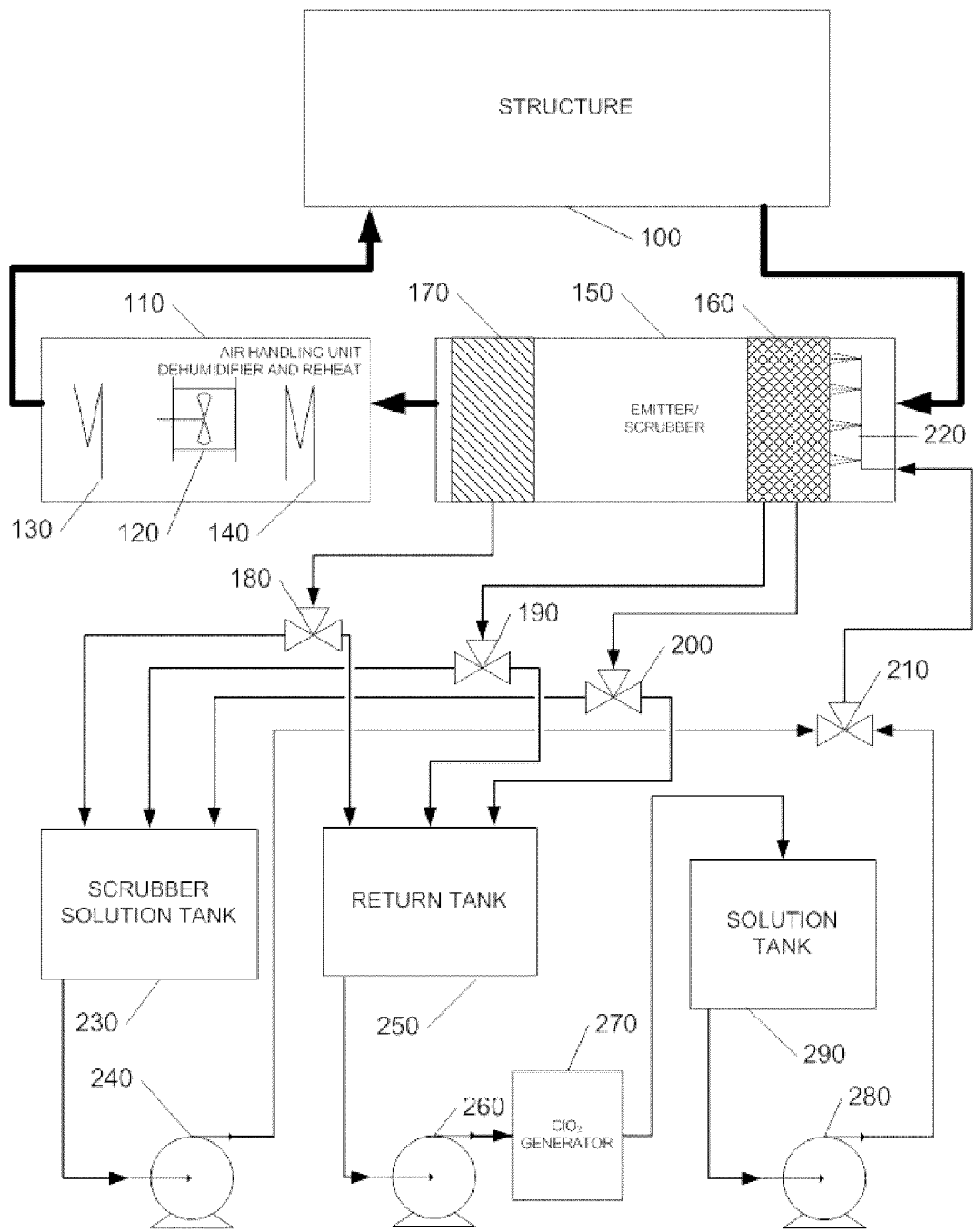
FIG. 9 is a schematic diagram of alternative apparatus suitable for use in the method of the invention.

For the scrubbing step, referring to FIG. 9D, the air flow through the emitter/scrubber 150 and air handling unit 110 is maintained by fan 120 with both the refrigeration coil 140 and the reheat coil 130 functioning, so that any humidity introduced in the air stream by the emitter/scrubber is removed before the air is returned to the structure.

First, the emitter/scrubber 150 has to be configured for use as a scrubber. Valves 180, 190 and 200 on the emitter/scrubber drains are configured so that any fluid from the emitter/scrubber drains into the scrubber solution tank 220. Valve 210 is configured so that the flow from pump 230 is delivered to the spray head 220 in the emitter/scrubber.

The scrubber tank 220 is filled with sufficient scrubber solution and at a concentration required to remove the quantity of chlorine dioxide gas that remains in the structure. The scrubber solution may be an alkalizing and dechlorinating agent or other chemical agent suitable for scrubbing chlorine dioxide gas from an air stream.

Pump 230 is switched on to pump scrubber fluid via valve 210 to the spray header 220 in the emitter/scrubber 150. An impingement bank 160 in the emitter/scrubber ensures intimate contact between the air stream containing chlorine dioxide gas and the scrubber solution. This contact enables chlorine dioxide gas to react with the scrubber solution and be removed from the air stream.

Scrubber solution drains from the emitter/scrubber impingement bank 160 to the scrubber solution tank 220 via valves 190 and 200. A mist eliminator 170 is utilized to remove water droplets from the air leaving the emitter/scrubber. Liquid taken from the air by mist eliminator 170 drains back into the scrubber solution tank 220 via valve 180.

The scrubber solution is pumped through the emitter/scrubber, and the air from the structure is recirculated through the emitter/scrubber until the measured concentration of chlorine dioxide gas in the air in the structure has been reduced to below the target concentration.

To adequately contain all the volume of liquid introduced to the system by, for example, chemicals used for the generation of chlorine dioxide, or water used for flushing the systems, the return tank 250, solution tank 290 and scrubber solution tank 230 are sized for sufficient volume to contain all the introduced liquids.

As described in U.S. application Ser. No. 11/576,498 and 11/270,973, the disclosures of which are incorporated herein by reference, for some gas phase applications the system may need to be configured to increase the relative humidity to a target value in the enclosed space to be fumigated.

Generation and Introduction of Chlorine Dioxide into Enclosed Space

Because chlorine dioxide is not stable at partial pressures over 83 millimeters of mercury, it is not available for purchase in high-pressure gas cylinders. Therefore chlorine dioxide gas must be generated at the decontamination site for subsequent introduction into an enclosed space to be fumigated. In general, chlorine dioxide solutions can be produced by treatment of chlorite salt solutions (e.g. $NaClO_2$) with an acid solution to produce acidic solutions that contain $ClO_2$, which can be then be flushed as a gas into water to produce aqueous $ClO_2$. Other precursors such as sodium chlorate can also be used.

Several chemical means of generating chlorine dioxide and their corresponding chlorine dioxide precursor chemicals are known in the art, and the choice of suitable means and chemicals is within the abilities of those skilled in the art. Exemplary chemical means of generating chlorine dioxide are disclosed in U.S. Pat. Nos. 4,689,169 (Mason et al.), 5,204,081 (Mason et al.), 5,227,306 (Eltomi et al.), 5,258,171 (Eltomi et al.), 5,965,004 (Cowley et al.), and 6,645,457 (Mason et al.) the disclosures of which are incorporated herein by reference. Because the goal is to eliminate corrosion, the chlorine dioxide should be of the highest possible purity. Specifically, chlorine gas should be present in the introduced chlorine dioxide gas at a level less than about 5%, preferably less than about 0.5%.

In one embodiment, the present invention provides a process that comprises producing chlorine dioxide by using an apparatus such as a chlorine dioxide generator, e.g. as disclosed and claimed in U.S. Pat. No. 6,468,479, the disclosure of which is incorporated herein by reference. The chlorine dioxide is generated either directly as a gas, or preferably as an aqueous (or other suitable liquid carrier) chlorine dioxide mixture. The generator is preferably run using an excess of sodium chlorite to reduce the possibility of generating chlorine gas as an impurity. Other generally accepted methods for generating chlorine dioxide can be found in, for example, U.S. Patent Pub. No. 2006/0068029 (U.S. patent application Ser. No. 11/131,021), the disclosure of which is incorporated herein by reference.

In another embodiment, the same equipment described in the above climatization step and shown in FIGS. 6-8 is used to a) introduce the chlorine dioxide gas into the volume requiring remediation, b) distribute the introduced chlorine dioxide gas within the volume, and c) maintain the chlorine dioxide gas within the volume at a concentration and for a sufficient duration to permit the gas to penetrate included contents as required for fumigation.

Aspects of this method are described in U.S. patent application Ser. No. 11/576,498, the disclosure of which is incorporated herein by reference.

In particular, the generated chlorine dioxide is transferred directly or alternatively, indirectly via a storage tank, to the emitter. In one preferred embodiment, the emitter is an apparatus such as the stripper discussed above and shown in FIGS. 6-8. The emitter is operated to maintain the gaseous chlorine dioxide concentration substantially below the explosion limit of chlorine dioxide in the air. In a further embodiment, the emitter is a combined emitter/scrubber as described above and shown in FIG. 9

As discussed above, throughout this step the relative humidity must be maintained at the target percentage for the particular application. Therefore, the climatization to achieve the target relative humidity (i.e. via de-humidification or humidification) and the remediation are performed simultaneously using the same apparatus by the appropriate adjustment in the temperature of chlorine dioxide solution, or by using an air handling unit that combines dehumidification and air reheating.

In addition to controlling the relative humidity in the enclosed space by controlling the humidity and temperature, one of ordinary skill in the art will recognize that illumination levels may also be reduced within the enclosed space, preferably to substantial darkness, to minimize the decomposition of chlorine dioxide to chlorine. The process is monitored with the use of an infrared camera or similar device. Temperature, relative humidity, concentration of decontamination agent, and contact time typically will be measured and recorded throughout the decontamination process.

Next, the variable generation rate of chlorine dioxide gas is initiated. The initial rate is high to provide sufficient chlorine dioxide to penetrate the various materials within the volume requiring remediation. This rate is predetermined to accommodate the material demand as well as to provide the initial charge of the volume requiring remediation to a predetermined chlorine dioxide residual level. The chlorine dioxide generation rate is then reduced appropriately to maintain the predetermined chlorine dioxide concentration in the air of the volume requiring remediation for a predetermined time. This can be achieved by various means, for example, lowering the concentration of chlorine dioxide in the solution that is fed to the emitter, or lowering the flow rate of the chlorine dioxide solution to the emitter.

The chlorine dioxide gas concentration is determined to compensate for the decay or loss rate from the volume requiring remediation. The volume requiring remediation is preferably to be at slightly negative pressure to areas outside of it, and the volume may be sealed off through the use of a strippable sealant, for example, a hardenable foam. In addition, the volume to be remediated can be enclosed within a substantially light impervious tent while undergoing remediation so as to avoid light-induced degradation of the introduced chlorine dioxide gas. In another embodiment, the tent is substantially impervious to gas.

Once the required time weighted average concentration and contact time are attained, then the generation of chlorine dioxide is stopped. In the next step, the generator, storage and emitter are purged with fresh water. Subsequently the water may be injected with an alkalizing and dechlorinating agent or other agent that will scrub the chlorine dioxide. This scrubbing solution is then fed to the emitter and with the blowers still in operation, and the emitter begins to scrub chlorine dioxide out of the environmental air composition within the volume that has been remediated.

Alternatively, the chlorine dioxide can be scrubbed from the environmental air by passing the air through a separate scrubber system containing water injected with an alkalizing and dechlorinating agent or other agent that will scrub the chlorine dioxide. This process is continued until the environmental air composition within the volume that has been remediated is returned to acceptable limits for reopening the exterior environment to re-habitation.

The emitters can be located inside or outside of the volume requiring remediation. However, it is highly preferred to locate the emitter inside the volume requiring remediation, since then no contaminated air is allowed to leave the volume requiring remediation.

Example 1

Laboratory Testing

In two identical chamber tests, samples of various metals known to be susceptible to corrosion by chlorine dioxide were placed along with three log (log 103) spore strips containing 1000 spores of *Bacillus atrophaeus* and three log (log 103) spore strips containing 1000 spores of *Claustridium* sporogonies. The samples included finishing nails, razor blades, paper clips, and metal files. On the first test, the samples were exposed to a concentration and time (CT) of chlorine dioxide for a total of 250 ppmv/hours at a relative humidity of 75%. The second test was identical except that the humidity was held between 45 and 50% relative humidity for the period of the test. Upon completion of exposure the metal samples were evaluated and the spore strips were cultured for growth. On each test there was no growth on any of the spore strips. Under the 75% relative humidity test conditions all of the test coupons showed moderate to severe rusting and corrosion. None of the test coupons at the 45 to 50% relative humidity demonstrated rusting or corrosion.

Example 2

Field Testing

A 2500-square foot building structure was encapsulated and prepared for treatment with chlorine dioxide gas. The structure was maintained under a negative pressure by withdrawing from 50 to 100 CFM of air from the structure throughout the treatment process. The withdrawn air was scrubbed though carbon filters to prevent the discharge of chlorine dioxide. Temperature and relative humidity were monitored at six locations throughout the structure. An external six ton HVAC system was connected to the home to provide temperature and humidity control.

Ten (10) locations within the building structure were sampled for bacterial growth prior to the treatment. Nine (9) of the locations tested positive for Sulfate Reducing Bacteria on the wallboard backing paper. Six log (log 106) and three log (log 103) spore strips of *B. atrophaeus* were embedded into sealed wall cavities to evaluate chlorine dioxide penetration. Ten (10) samples of metallic objects and coupons were placed within the treatment zone. The metal objects and coupons were all materials that were known to be sensitive to chlorine dioxide exposure at higher relative humidity levels. The coupons were scuffed mild steel and high carbon steel. The items were uncoated cast steel, files, razor blades, and uncoated finishing nails.

A six thousand lb per day (6000 lb/day) chlorine dioxide system with the appropriately sized gas strippper was used to apply chlorine dioxide to the building structure. Chlorine dioxide gas was added to the structure to achieve a concentration ranging from 2800 to 3800 ppmv throughout the structure. For a twelve hour period chlorine dioxide was added to the structure to maintain these concentrations. During the treatment period the relative humidity was maintained within the structure between 32 and 45%. The total chlorine dioxide (CT) exposure of the structure was 37,000 ppmv/hours.

All of the six log (log 106) and three log (log 103) spore strips were deactivated, and all ten (10) wall sample locations tested negative for bacterial growth post treatment. With the exception of the razor blade which showed slight rusting, none of the other test materials demonstrated rusting or corrosion.

Example 3

Field Testing

A structure was prepared for fumigation with chlorine dioxide gas by enclosing the structure within an envelope, installing a scrubbing system upon the structure to maintain a negative pressure within the envelope, and installing temperature and humidity control equipment to maintain environmental levels. The structure had a footprint of approximately 3200 square feet and a volume of 53000 cubic feet. During the treatment the structure was maintained at relative humidity levels ranging from 38 percent to 56 percent. Chlorine dioxide was added continuously for about 14 hours to maintain an average concentration of about 3800 ppmv. The total treatment of the structure was an average of 52,000 ppmv hours of chlorine dioxide.

Prior to the treatment of 10 locations, the drywall was sampled to determine the presence of bacterial growth by culture for anaerobic, aerobic, and sulfate reducing bacteria. All locations exhibited growth on the wallboard surface, within the front and back wallboard paper, and within the core of the gypsum. All locations exhibited bacterial growth. Six log spore strips were inserted deep into the wall cavities prior to the fumigation. All wall penetrations made during sampling were sealed with "plumber's plugs" prior to fumigation.

Post fumigation, no bacterial growth was observed at any of the sample locations. All spore strips were completely inactivated. Post fumigation numerous types of insects and arachnids, including ants, flies, larvae, bees, termites, and spiders were observed dead throughout the structure. Numerous geckos on the walls and floors within the fumigated volume were also found dead post fumigation.

Metals such as exposed, scuffed mild steel and high carbon steel known to be sensitive to chlorine dioxide fumigation at high humidities were examined at six hours, thirty days, and sixty days following fumigation. No evidence of corrosion due to the fumigation was observed.

Example 4

Field Testing

Five residential structures were selected to be treated with chlorine dioxide gas. The size of these structures ranged from 2400 to 5000 square feet, with volumes under roof ranging from 35000 to 70000 cubic feet. Each of the homes was inspected prior to treatment with chlorine dioxide for signs of rusting or corrosion prior to treatment with chlorine dioxide gas. Materials that are known to be sensitive to chlorine dioxide were inspected in detail. These items were picture wall hangers, finishing nails, inexpensive cabinet hinges, and abraded screw heads. Pictures were taken of all of these items prior to fumigation. None of these items demonstrated corrosion or rust prior to fumigation.

Each of the structures was fumigated with chlorine dioxide gas at concentrations from 1500 ppmv to 4500 ppmv chlorine dioxide. The total chlorine dioxide concentration times time (CT) ranged from 9000 $ppm_v$ hours to 54,000 $ppm_v$ hours. All of the structures were inspected immediately post fumigation and 30 days after fumigation. No corrosion or rusting was observed in any of the structures. All of the highly sensitive materials were corrosion-free post fumigation on the immediate and 30 day evaluations.

Humidity measured in the structures prior to fumigation ranged from 65% to 80%. Immediately prior to fumigation, the relative humidity levels were adjusted to 48% or less using a humidity control system. The process used a cooling coil to remove moisture from the air and a reheating coil to maintain temperature within the structure.

Temperatures within the structures during fumigation ranged from 65° F. to 85° F. Humidity was maintained throughout the treatment process in the range of 43% to 54%. Post fumigation the chlorine dioxide was removed from the buildings to a concentration of less than 0.1 $ppm_v$ with a wet scrubbing system. Humidity during the scrubbing cycle ranged from 30% to 54% relative humidity.

During post scrubbing of the chlorine dioxide, the structures were purged with outside air for a period of 72 hours. The purge air temperature ranged from 35° F. to 75° F. and from 40% to 85% relative humidity. Penetration of chlorine dioxide throughout the structure was verified by culture tests of the drywall core and by the insertion of "spore strips" within the structure walls. Chlorine dioxide kill, and thus penetration, was demonstrated on all of the core samples and all of the inserted spore strips on all of the tests and all of the structures.

Example 5

Chinese Wallboard Contamination

INTRODUCTION

Media reports indicate widespread concern exists among homeowners and apartment dwellers living in structures containing Chinese wallboard that the wallboard gives off gases that can corrode copper pipes, blacken jewelry and silverware, and possibly sicken people.

A study funded by the Florida Department of Health (FDOH) confirmed that Chinese wallboard does indeed have the potential to evolve a number of reduced-sulfur gases under temperature and relative humidity (RH) conditions common in the southeastern US. The FDOH study identified hydrogen sulfide, carbonyl sulfide and carbon disulfide as evolving from Chinese wallboard samples when exposed to elevated RH levels. None of these gases has been shown to evolve from comparable American drywall products at any RH level. A separate analysis of Chinese wallboard by the US Environmental Protection Agency (USEPA) did not show the presence of any of these three compounds in the Chinese drywall materials themselves.

One technology that shows great promise for solving the Chinese wallboard problem is a gaseous chlorine dioxide ($ClO_2$) fumigation process originally developed by Sabre Technical Services, LLC (Sabre) while assisting USEPA and the US Postal Service (USPS) in devising a technical solution to widespread *Bacillus anthracis* (i.e. anthrax) contamination present in buildings following the anthrax attacks of 2001. Sabre's $ClO_2$ fumigation technology was used to eliminate anthrax contamination from the Hart Senate Office Building and USPS Curseen-Morris Processing and Distribution Center (P&DC) in Washington, D.C., the USPS Trenton P&DC in Hamilton Township, N.J. and the former American Media, Inc. Building in Boca Raton, Fla. The size of these $ClO_2$ fumigation applications ranged from a low of 100,000 cubic feet ($ft^3$) to a high of over 14 million $ft^3$.

Preliminary test work conducted at Sabre's research and development facility in Slingerlands, N.Y. using samples of Chinese wallboard obtained from various affected structures indicated that $ClO_2$ did indeed hold potential as remedial treatment agent for installed wallboard material. As such, a field technology demonstration project was scheduled at a problem residence in Ft. Myers, Fla. on Jun. 6, 2009 to confirm laboratory observations regarding penetration of $ClO_2$ in an actual affected structure.

Project Objectives

Objectives of this field technology demonstration project were to: 1.) document that the $ClO_2$ fumigation process would result in gas penetration throughout the structure leading to effective elimination of odorous reduced-sulfur compounds; 2.) verify that $ClO_2$ would not cause unacceptable changes within a treated structure in terms of metal corrosion or material bleaching; and 3.) further investigate the ability of $ClO_2$ to inactivate sulfate-reducing bacteria (SRBs) present within wallboard material in case it was eventually determined that they played a meaningful role in the reduced-sulfur gas evolution problem.

Efficacy Sampling Approach

A major complication in determining success of $ClO_2$ in eliminating reduced-sulfur compounds from an affected structure is the difficulty of measuring and analyzing these gases at the low concentrations they are present at within the structure. Sabre used various surrogate measures to document the efficacy of $ClO_2$ gas in ridding the test structure of reduced-sulfur compounds.

Gas Penetration—The effects of substrate oxidation occur before effective microbial kill takes place during ClO2 treatment. A certain minimum "concentration×time" (CT) value must be first accumulated in order to overcome the natural oxidative "demand" of substrate materials prior to achieving microbial kill. This principal forms the basis for decision-making when calculating dosing levels in both liquid and gaseous ClO2 applications. Therefore, to the extent that pervasive microbial kill can be shown throughout a structure, including inside wall cavities and within substrate materials themselves, it is reasonable to conclude that reduced-sulfur compounds in those locations have also been effectively oxidized.

In order to demonstrate that pervasive microbial kill took place throughout the test structure, and by implication effective oxidation of reduced-sulfur compounds, Sabre's testing approach included two surrogate measures of microbial kill. First, Chinese wallboard has been shown to contain elevated SRB levels compared to conventional wallboard, particularly in the unpainted paper layer. Thus, testing of SRB levels in this layer both pre- and post-treatment provides a good indication of how well $ClO_2$ gas penetrated into the wallboard and oxidized any reduced-sulfur compounds present in the material. Second, biological indicator (BI) spore strips containing a known titer of *Bacillus atrophaeus* bacterial spores were deployed inside wall cavities at representative locations throughout the structure. The *B. atrophaeus* species is widely recognized as being the most difficult to inactivate with $ClO_2$ gas. Pervasive inactivation of BIs in "hard to reach" areas of the structure (i.e. inside wall cavities) thus indicates that pervasive oxidation of reduced-sulfur compounds also occurred throughout the structure.

Subjective Odor Elimination—Reduced-sulfur compounds odors are extremely noxious and can be detected by the human olfactory (i.e. odor) sense at levels which are at or below the detection limits of sophisticated analytical instruments. As such, the olfactory senses of both Sabre personnel and independent observers were employed both pre- and post-treatment to gauge the effectiveness of ClO2 in ridding the test structure of reduced-sulfur compound odors.

Elimination of Copper Blackening Effect—Reduced-sulfur compounds have been shown to blacken and corrode copper materials in affected structures over time. Exposure durations in contaminated buildings that result in blackening occurring have been reported as being from one to four weeks under typical environmental conditions. Untarnished copper coupons were placed within the test structure post-treatment and were monitored over time.

Test Structure

A Courtyard Home with a "Berkshire Floor Plan" located at 5683 Kensington Loop in The Residences at Bell Tower Park in Fort Myers, Fla. was used as the field technology demonstration site. This 2,429 square foot two-story home consists of 3 bedrooms, 3.5 baths, a kitchen, grand room, dining room, laundry room and an attached 2-car garage. This home also has an adjacent 286 square foot guest cabana consisting of 1 bedroom, 1 bathroom and a small kitchen. The main home and guest cabana are connected by a private courtyard with a screen ceiling enclosure, brick foundation and small spa.

The entire structure, including main home, guest cabana and private courtyard was enclosed with impermeable polyethylene sheeting material during the fumigation to prevent release of $ClO_2$ gas to the surrounding environment.

Test Methods and Materials

Efficacy of the $ClO_2$ fumigation process was monitored in several different ways. Key process parameters were monitored throughout the fumigation period to ensure that target treatment conditions were achieved within the affected structure. These process parameters included temperature, RH, $ClO_2$ concentration and fumigant dose, which is expressed in terms of $ClO_2$ CT "credits."

Pre- and post-treatment SRB samples were collected from wallboard material throughout the structure to assess efficacy of the $ClO_2$ gas in inactivating bacteria present within them, and thus oxidizing any reduced-sulfur compounds. BI spore strips were also placed in representative locations throughout building wall cavities to document that pervasive gas penetration occurred throughout the structure.

Visual and olfactory observations were made by Sabre personnel, as well as by independent parties, on a number of important variables including corrosivity potential of $ClO_2$ on copper and other metals, bleaching potential of $ClO_2$ on carpeting and odor presence within the structure both pre- and post-treatment.

Temperature and RH—Temperature and RH conditions within the structure were monitored throughout the fumigation at four representative locations. Each monitored location was deemed to be a potential problem area for controlling temperature and RH conditions based on the home's heating, ventilation and air conditioning (HVAC) system and airflow movement characteristics. Selected monitoring locations were in the 1st floor master suite closet; inside the attic access point in the garage; in the guest cabana kitchen; and inside the attic access point in the 2nd floor suite #2 closet.

The target temperature and RH conditions chosen for the fumigation were a temperature of 80° F.±5° F. and an RH level of 45%±5% at all monitoring locations.

Temperature and RH levels were monitored through use of HOBO® Model U12-011 TEMP/RH Data Loggers manufactured by Onset Computer Corporation. The instrument temperature measuring range is −4 to 158° F. with an accuracy of ±0.63° F. The RH measuring range is 5% to 95% with an accuracy of ±2.5%. Temperature and RH measurements were monitored on a real-time basis and logged at 5-minute intervals throughout the fumigation process.

ClO2 Concentrations and CT Values—ClO2 concentration levels were monitored throughout the fumigation process at the same four representative locations selected for temperature and RH monitoring. These locations were, again, selected based on knowledge of the home's HVAC systems and airflow movement characteristics.

The target $ClO_2$ parameters selected for this project were an average concentration of 500 $ppm_v$ or more and a CT value not less than 2,000 $ppm_v$ nor more than 9,000 $ppm_v$ at all monitoring locations. Monitoring of $ClO_2$ concentrations began shortly after the gas was first introduced into the structure and continued at periodic intervals throughout the fumigation process.

Monitoring was accomplished by means of a sample collection system constructed of one-quarter inch inside diameter high-density polyethylene (HDPE) tubing. The HDPE tubing was run from the four designated monitoring locations to a central sampling manifold located outside the building in a mobile laboratory facility. Samples were collected and analyzed by trained technicians. Air flowed continuously to the sampling manifold so that samples represented existing conditions within the building at the time they were taken. A vacuum pump was placed on the downstream side of the sampling manifold to move air through the system and return it to the structure on a continuous basis throughout the fumigation process.

Samples were collected from the sampling manifold via impingement of two liters of air at a flow rate of 1.0 liter per minute through 15 milliliters of a strongly buffered pH 7 potassium iodide solution (modified US Occupational Safety and Health Administration Method ID126SGX). Once collected, samples were analyzed by colorimetric titration, using a 0.1 normal sodium thiosulfate solution as the titrant (modified American Water Works Association Method 4500-$ClO_2$-E and modified 2-step version of same).

A fumigation $ClO_2$ CT dose "clock" was started for each of the four co-located monitoring points when temperature and RH conditions had equilibrated in their desired ranges and gas introduction into the structure had begun. Once started, each CT clock accumulated $ClO_2$ exposure "credit" until the target dose level had been achieved at each monitoring location, at which time the fumigation was deemed complete.

SRBs—The efficacy of ClO2 gas in eliminating SRBs from Chinese wallboard material was evaluated by collecting samples of unpainted wallboard paper located inside wall cavities of the home prior to, and immediately after, ClO2 exposure. Unpainted wallboard paper from wall cavities was chosen for SRB testing because preliminary laboratory work done at Sabre's Slingerlands, N.Y. laboratory facility had shown SRBs to be concentrated in this media.

Pre-treatment wallboard paper samples were collected by drilling a two-inch circular core at selected wall and ceiling locations. To avoid damaging vapor barriers present within the home, samples were not collected from any bathroom or laundry room locations. Sample locations were selected to be representative wall cavities within the structure most likely to contain conditions conducive to SRB growth. In total, 20 sample locations were selected. Nine were wall cores and eleven were ceiling cores.

The wallboard holes created through SRB sampling were each sealed using a two-inch rubber expansion plug in order to ensure that $ClO_2$ gas would not penetrate into wall cavities as a consequence of sampling activities.

Post-treatment wallboard paper samples were collected by drilling an identical two-inch circular core approximately one inch away from each of the 20 pre-treatment sample locations.

Following collection, wallboard paper samples were sent to EMLab P&K for independent third party analysis using Method C461—Sulfate Reducing Bacteria Analysis—Presence/Absence.

BI Spore Strips—BI spore strips, each containing an approximate $2.5 \times 10^3$ titer of *B. atrophaeus* spores, were placed within wall cavities of the structure at the same 20 locations where wallboard samples had been collected, prior to insertion of the 2-inch expansion plugs. The *B. atrophaeus* species was selected due to its historical use as a biological indicator for $ClO_2$ fumigations Spore strips are thin cellulose pads that have been impregnated with a defined titer of bacterial spores. Each spore strip is encased in a Tyvek® pouch to allow for effective penetration of fumigant gas yet protect the strip from contamination by external sources. The BIs were obtained from SGM Biotech Inc., 10 Evergreen Drive, Suite E, Bozeman, Mont. (Lot #ACD-113e). All BIs were supplied from the same product batch in order to ensure uniformity in spore titer. Relevant production QA/QC data for the specific lot number have been kept on file for future reference.

All BIs were retrieved promptly following fumigation and sent to Sabre's Slingerlands, N.Y. laboratory facility for analysis. Each spore strip was aseptically placed in a growth media tube containing 15 milliliters of trypticase soy broth (BD Diagnostics product #221823, Lot #7337460) and incubated at 37° C. Spore strips were evaluated daily for the presence or absence of indicator organism growth for a total of seven days.

Visual and Olfactory Observations

The corrosivity potential of $ClO_2$ on metals and bleaching potential of $ClO_2$ on household carpeting were evaluated through pre- and post treatment visual observations made throughout the structure.

Corrosivity potential was assessed by observation of typical metal items present within the structure (e.g. screws, door hinges, HVAC system components, etc.). Several pieces of copper pipe were also placed on the Café countertop for the duration of fumigation to verify that $ClO_2$ would not cause any adverse effects such as corrosion or discoloration. Each piece of copper was "scuffed" clean prior to fumigation to ensure that any changes in the metal due to $ClO_2$ exposure would be readily recognizable. Photographs were taken of the copper pipe pieces before and after treatment to document visual observations made.

Bleaching potential of $ClO_2$ was assessed by observation of carpet color and brightness throughout the structure both pre- and post-treatment. A piece of carpeting was also removed from a closet within the structure prior to fumigation and used for direct visual comparison with treated carpet following completion of the process.

Odor levels emanating from within the structure were observed both pre- and post-treatment for the "putrid" characteristic commonly associated with reduced-sulfur gases such as hydrogen sulfide, carbonyl sulfide and carbon disulfide that have been definitively shown by an FDOH study as being released from Chinese wallboard.

Quality Control

BI Spore Strips—Positive control BIs were submitted to the Sabre laboratory for viability testing along with the fumigated BIs in a ratio of approximately one positive control sample for every 10 treated samples, for a total of two positive controls. Positive controls are untreated (i.e., not fumigated) BIs of identical composition that are submitted to the laboratory along with the exposed BIs. Positive controls provide evidence of BI product quality as well as evidence that appropriate conditions for growth of the surrogate test organism were achieved. The positive control samples were handled, packaged and shipped in the same manner as the actual samples from the building, except that the positive controls were not subjected to the fumigant gas.

Results

Temperature & RH—Raw temperature and RH data were exported from the HOBO® data loggers into a Microsoft Corporation Excel® spreadsheet for purposes of calculating mean temperature and RH levels for each monitoring location. These mean temperature and RH values (±one standard deviation) are shown in Table 1.

TABLE 1

Temperature & RH Data Summary

| | | Actual | | | |
|---|---|---|---|---|---|
| | Target | Line 101 Master Suite Closet | Line 102 Garage Attic Access | Line 103 2nd Floor Attic Access | Line 104 Guest Cabana |
| Temp (° F.): | 80 | 76.5 (±1.9) | 81.1 (±5.8) | 82.6 (±5.2) | 76.9 (±2.4) |
| RH (%): | 45 | 47.8 (±1.0) | 48.2 (±1.9) | 45.1 (±2.6) | 51.7 (±0.8) |

Monitoring data showed that temperature and RH were maintained close to target levels throughout the fumigation. The slightly elevated RH level observed in the Guest Cabana (51.7%) was believed to be the result of water present in the courtyard spa.

ClO2 Concentrations and CT Values—Raw sample collection and analytical data were entered into a Microsoft Corporation Excel® spreadsheet for purposes of calculating mean ClO2 concentrations and accumulated CT values for each monitoring location. These mean ClO2 concentration and CT values (±one standard deviation) are shown in Table 2.

TABLE 2

$ClO_2$ & CT Data Summary

| | | Actual | | | |
|---|---|---|---|---|---|
| | Target | Line 101 Master Suite Closet | Line 102 Garage Attic Access | Line 103 2nd Floor Attic Access | Line 104 Guest Cabana |
| Time (hours): | 4+ | 13 | 13 | 13 | 13 |
| $ClO_2$ ($ppm_v$): | 500+ | 695 (±298) | 685 (±267) | 475 (±218) | 825 (±340) |
| CT ($ppm_v$-hours): | 2000-9000 | 8090 | 8061 | 5336 | 9727 |

Monitoring data showed that $ClO_2$ concentrations and CT values were maintained within target ranges established for the fumigation. A mean $ClO_2$ concentration slightly less than 500 $ppm_v$ was maintained at the $2^{nd}$ floor attic access point, however a corresponding CT greatly in excess of the 2,000 $ppm_v$-hour minimum was also achieved at this location.

SRBs—SRB growth test results for the 20 unpainted wallboard paper samples collected from within wall cavities before and after fumigation and sent to EMLab P&K are summarized in Table 3.

TABLE 3

SRB Summary Data

| Location Description | Location ID | Before | After |
|---|---|---|---|
| Wall core—Grand Rm | 1 | No Growth | No Growth |
| Wall core—Master Suite | 2 | No Growth | No Growth |
| Wall core—Dining Rm | 3 | No Growth | No Growth |
| Wall core—Master Suite | 4 | Growth | No Growth |
| Wall core—Kitchen | 5 | Growth | No Growth |
| Wall core—Leisure Rm | 6 | Growth | No Growth |
| Ceiling core—Garage | 7 | Growth | No Growth |
| Ceiling core—Garage | 8 | Growth | No Growth |
| Ceiling core—Café | 9 | Growth | No Growth |
| Ceiling core—Foyer | 10 | No Growth | No Growth |
| Ceiling core—Grand Rm | 11 | Growth | No Growth |
| Ceiling core—Master Suite | 12 | No Growth | No Growth |
| Ceiling core—Master Suite Closet | 13 | No Growth | No Growth |
| Wall core—Suite #2 | 14 | No Growth | No Growth |
| Wall core—Suite #3 | 15 | Growth | No Growth |
| Ceiling core—Suite #3 Closet | 16 | No Growth | No Growth |
| Ceiling core—Suite #2 Closet | 17 | Growth | No Growth |
| Ceiling core—Guest Cabana | 18 | Growth | No Growth |

TABLE 3-continued

SRB Summary Data

| Location Description | Location ID | Before | After |
|---|---|---|---|
| Wall core—Guest Cabana | 19 | Growth | No Growth |
| Ceiling core—Guest Cabana | 20 | Growth | No Growth |
| Negative Control | — | — | No Growth |

The SRB growth data indicated a widespread presence of SRBs within the unpainted wallboard paper prior to fumigation. Twelve of 20 sample locations were found to be positive for SRBs prior to $ClO_2$ treatment. Following treatment, all 20 locations were determined to be negative for SRB growth.

BI Spore Strips—Viability test results for the 20 BI spore strips placed within wall cavities of the structure during fumigation are shown in Table 4.

TABLE 4

Spore Strip Summary Data

| Location Description | Location ID | Result |
|---|---|---|
| Wall core—Grand Rm | 1 | No Growth |
| Wall core—Master Suite | 2 | No Growth |
| Wall core—Dining Rm | 3 | No Growth |
| Wall core—Master Suite | 4 | No Growth |
| Wall core—Kitchen | 5 | No Growth |
| Wall core—Leisure Rm | 6 | No Growth |
| Ceiling core—Garage | 7 | No Growth |
| Ceiling core—Garage | 8 | No Growth |
| Ceiling core—Café | 9 | No Growth |
| Ceiling core—Foyer | 10 | No Growth |
| Ceiling core—Grand Rm | 11 | No Growth |
| Ceiling core—Master Suite | 12 | No Growth |
| Ceiling core—Master Suite Closet | 13 | No Growth |
| Wall core—Suite #2 | 14 | No Growth |
| Wall core—Suite #3 | 15 | No Growth |
| Ceiling core—Suite #3 Closet | 16 | No Growth |
| Ceiling core—Suite #2 Closet | 17 | No Growth |
| Ceiling core—Guest Cabana | 18 | No Growth |
| Wall core—Guest Cabana | 19 | No Growth |
| Ceiling core—Guest Cabana | 20 | No Growth |
| Positive Control | — | Growth |
| Positive Control | — | Growth |

The BI test results verified that pervasive, efficacious $ClO_2$ gas penetration occurred throughout the structure, including inside wall cavities, during fumigation. Each of 20 log $10^3$ Bacillus atrophaeus spore strips placed in very challenging locations within the wall cavities were found to be negative for surrogate test organism growth following $ClO_2$ treatment. Both positive control BI spore strip samples were found to be positive for indicator organism growth, thereby indicating that BI product quality was good and that appropriate conditions for growth of the surrogate test organism were achieved in the laboratory.

Visual and Olfactory Observations

Observations made of common metal items present within the structure following fumigation indicated no corrosive effect was visible from exposure to the $ClO_2$ gas. Similarly, no changes were observed in the pieces of copper pipe placed on the Café countertop, with the minor exception that some pieces appeared to have a "gold-like" tint following treatment.

Observations made of carpet color and brightness throughout the structure following fumigation indicated no meaningful bleaching effect had occurred from exposure to the $ClO_2$ gas. A direct side-by-side comparison of treated carpet with a piece of untreated carpet removed from the structure prior to fumigation confirmed this finding. It should be noted that each dye lot and color of carpet behaves differently and needs to be individually evaluated.

Putrid odors characteristic of reduced-sulfur compounds known to evolve from Chinese wallboard were readily apparent to both Sabre personnel and independent observers throughout the structure prior to fumigation, and were particularly strong in the garage and cabana areas. Following fumigation, a faint "swimming pool like" scent was present in the structure from use of $ClO_2$ gas, but the reduced-sulfur gas odors appeared to have been completely eliminated.

CONCLUSIONS

All process parameter targets, including temperature, RH, $ClO_2$ concentration and CT values, were achieved during this field technology demonstration project and all objectives were satisfied.

The $ClO_2$ fumigation process was shown capable of inactivating SRBs present within wallboard material, as well as BI spore strips embedded within wall cavities, thereby demonstrating the ability of $ClO_2$ gas to completely permeate an affected structure and oxidize reduced sulfur compounds at the CT values employed. In addition, it was demonstrated that $ClO_2$ would not cause unacceptable changes within a treated structure in terms of metal corrosion or material bleaching.

One of ordinary skill in the art will recognize that the invention described herein is not limited to a specific gas phase application of chlorine dioxide, but will cover a wide spectrum of fumigation and gas phase applications such as, but not limited to, Anthrax or other microbial decontamination, sterilization chambers in hospitals, mold remediation, wallboard remediation, and disinfection of medical waste. Furthermore, the present invention is not to be limited in scope by the specific embodiments described herein, but by the appended claims. The described embodiments are intended as illustrations of individual aspects of the invention, and functionally equivalent methods and components are within the scope of the invention. Indeed, various modifications of the invention, in addition to those shown and described herein will become apparent to those skilled in the art from the foregoing description and accompanying drawing. Such modifications are intended to fall within the scope of the appended claims.

| List of Acronyms | |
|---|---|
| BI | Biological Indicator |
| CFM | Cubic Feet Per Minute |
| $ClO_2$ | Chlorine Dioxide |
| CT | Concentration × Time |
| DFU | Dry Filter Unit |
| F | Fahrenheit |
| FDOH | Florida Department of Health |
| HDPE | High Density Polyethylene |
| HVAC | Heating, Ventilation and Air Conditioning |
| P&DC | Processing and Distribution Center |
| $ppm_v$ | Parts Per Million by Volume |
| RH | Relative Humidity |
| Sabre | Sabre Technical Services, LLC |
| SRBs | Sulfate-Reducing Bacteria |
| USEPA | US Environmental Protection Agency |
| USPS | US Postal Service |

The invention claimed is:

1. A method for gas phase application of chlorine dioxide within an enclosed volume comprising the steps of: climatizing the enclosed volume to a relative humidity equal to x (%); generating chlorine dioxide gas; and introducing the chlorine dioxide gas into the enclosed volume at a CT value of chlorine dioxide equal to y ($ppm_v$-hrs), wherein $y=6x^2-870x+32100\pm1000$, x being a number between 5 and 56 equal to the % RH.

2. A method for gas phase application of chlorine dioxide within an enclosed volume comprising the steps of: climatizing the enclosed volume to achieve a relative humidity (RH) in the range of about 5% to about 56%; generating chlorine dioxide gas; and introducing the chlorine dioxide gas at a concentration ranging from 25 $ppm_v$ to 10,000 $ppm_v$ for the appropriate time into the enclosed volume to achieve a CT value of chlorine dioxide equal to y ($ppm_v$-hrs); wherein $y=6x^2-870x+32100\pm1000$, x being a number between 5 and 56 equal to the % RH.

3. A method for gas phase application of chlorine dioxide within an enclosed volume, comprising the steps of:
   climatizing the enclosed volume to achieve a relative humidity (RH) in the range of about 5% to about 56%;
   generating chlorine dioxide gas; and
   introducing the chlorine dioxide gas under specified conditions of chlorine dioxide gas concentration and contact time, said conditions being effective to eliminate contaminants within said closed volume, and further to mitigate corrosion within said enclosed volume during said gas phase application wherein said introducing the chlorine dioxide gas comprises introducing the chlorine dioxide gas into the enclosed volume at a target CT value of chlorine dioxide approximately equal to a value of about y ($ppm_v$hrs), wherein $y=6x^2-870x+32100^+-1000$, x being equal to % RH.

4. The method of claim 3 wherein said relative humidity (RH) is in the range of about 35% to about 53%.

5. The method of claim 4 wherein said relative humidity (RH) is in the range of about 40% to about 52%.

6. The method of claim 5 wherein said relative humidity (RH) is in the range of about 45% to about 50%.

7. The method of claim 6 wherein said relative humidity (RH) is in the range of about 45% to about 48%.

8. The method of claim 3 wherein said contaminants within said enclosed volume are selected from the group consisting of: bacteria, spores, molds, mycotoxins, allergens, insects, larvae, arachnids, lizards, and combinations thereof.

9. The method of claim 3 wherein said enclosed volume comprises objects selected from the group consisting of metallic objects, non-metallic objects, and combinations thereof.

10. The method of claim 9 wherein said metallic objects are formed from metals selected from the group consisting of steel, aluminum, iron, copper, chromium, lead, and combinations thereof.

11. The method of claim 9 wherein said non-metallic objects are formed from materials selected from the group consisting of wood, brick, stone, concrete, ceramic tile, ceiling tile, carpet, woven fabric, and combinations thereof.

12. The method of claim 3 wherein said introducing the chlorine dioxide gas comprises: introducing chlorine dioxide gas into the enclosed volume at a CT value of about 29,000 $ppm_v$-hrs to about 1000 $ppm_v$-hrs.

13. The method of claim 3 wherein said introducing the chlorine dioxide gas comprises: introducing chlorine dioxide gas into the enclosed volume at a concentration of about 25 $ppm_v$ to about 10,000 $ppm_v$.

14. The method of claim 13 wherein said chlorine dioxide gas is at a concentration of about 500 $ppm_v$ to about 3,000 $ppm_v$.

15. The method of claim 14 wherein said climatizing the enclosed volume is carried out at a temperature of about 18° C. (65° F.) to about 29° C. (85° F.).

16. The method of claim 3 wherein said climatizing the enclosed volume is carried out at a temperature of about 10° C. (50° F.) to about 32° C. (90° F.).

* * * * *